United States Patent
Monson et al.

(10) Patent No.: US 8,979,769 B2
(45) Date of Patent: *Mar. 17, 2015

(54) BIOPSY DEVICE WITH VACUUM ASSISTED BLEEDING CONTROL

(71) Applicant: Devicor Medical Products, Inc., Cincinnati, OH (US)

(72) Inventors: Gavin M. Monson, Oxford, OH (US); Trevor W. V. Speeg, Williamsburg, OH (US); Bennie Thompson, Cincinnati, OH (US); Robert F. Weikel, Hamilton, OH (US); Michael R. Ludzack, Maineville, OH (US); John A. Hibner, Mason, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 102 days.

This patent is subject to a terminal disclaimer.

(21) Appl. No.: 13/760,364

(22) Filed: Feb. 6, 2013

(65) Prior Publication Data
US 2013/0150750 A1  Jun. 13, 2013

Related U.S. Application Data

(63) Continuation of application No. 13/025,366, filed on Feb. 11, 2011, now Pat. No. 8,568,335, which is a continuation of application No. 11/424,576, filed on Jun. 16, 2006, now Pat. No. 7,918,804, which is a continuation-in-part of application No. 11/198,558, filed on Aug. 5, 2005, now Pat. No. 7,867,173.

(51) Int. Cl.
*A61B 10/00* (2006.01)
*A61B 10/02* (2006.01)
*A61B 17/00* (2006.01)

(52) U.S. Cl.
CPC .......... *A61B 10/0266* (2013.01); *A61B 10/0275* (2013.01); *A61B 10/0283* (2013.01); *A61B 2010/0225* (2013.01); *A61B 2017/0046* (2013.01)
USPC ........................................ 600/568

(58) Field of Classification Search
CPC .......... A61B 10/0275; A61B 10/0283; A61B 10/0266; A61B 2017/0046; A61B 2010/0225
USPC ......... 600/562–568; 606/167, 170; 604/1, 11, 604/358, 393, 904, 907
See application file for complete search history.

(56) References Cited

U.S. PATENT DOCUMENTS

| | | |
|---|---|---|
| 2,853,071 A | 9/1958 | Saffir |
| 3,630,192 A | 12/1971 | Jamshidi |

(Continued)

FOREIGN PATENT DOCUMENTS

| | | |
|---|---|---|
| EP | 0890339 | 1/1999 |
| EP | 0 995 400 | 4/2000 |

(Continued)

OTHER PUBLICATIONS

U.S. Appl. No. 60/869,736, filed Dec. 13, 2006, Hibner.

(Continued)

*Primary Examiner* — Brian Szmal
(74) *Attorney, Agent, or Firm* — Frost Brown Todd LLC

(57) ABSTRACT

A biopsy device includes an elongate needle, a proximal portion, a cutter, and a vacuum conduit. The elongate needle defines an internal passage and includes a distal end and a first plurality of openings along an exterior surface of the elongate needle in communication with the internal passage. The first plurality of openings are sized to admit fluid and to resist the prolapse of tissue. The proximal portion is attached to the elongate needle and is positionable to insert the elongate needle into tissue. The cutter is reciprocally received by the elongate needle to sever a tissue sample received in the elongate needle. The cutter includes a cutter tube with a second plurality of openings in communication with the internal passage of the elongate needle. The vacuum conduit is attached to the proximal portion in communication with the internal passage and is coupled to a vacuum source.

20 Claims, 18 Drawing Sheets

(56) References Cited

U.S. PATENT DOCUMENTS

| | | |
|---|---|---|
| 3,719,086 A | 3/1973 | Bannister et al. |
| 3,994,297 A | 11/1976 | Kopf |
| 4,051,852 A | 10/1977 | Villari |
| 4,600,014 A | 7/1986 | Beraha |
| 4,782,833 A | 11/1988 | Einhorn |
| 5,234,000 A | 8/1993 | Hakky et al. |
| 5,406,959 A | 4/1995 | Mann |
| 5,439,457 A | 8/1995 | Yoon |
| 5,526,822 A | 6/1996 | Burbank et al. |
| 5,532,168 A | 7/1996 | Marantz |
| 5,601,585 A | 2/1997 | Banik et al. |
| 5,645,209 A | 7/1997 | Green et al. |
| 5,649,547 A | 7/1997 | Ritchart et al. |
| 5,769,086 A | 6/1998 | Ritchart et al. |
| 5,775,333 A | 7/1998 | Burbank et al. |
| 5,873,967 A | 2/1999 | Clark et al. |
| 5,876,329 A | 3/1999 | Harhen |
| 5,928,164 A | 7/1999 | Burbank et al. |
| 5,964,716 A | 10/1999 | Gregoire et al. |
| 5,980,469 A | 11/1999 | Burbank et al. |
| 6,007,497 A | 12/1999 | Huitema |
| 6,017,316 A | 1/2000 | Ritchart et al. |
| 6,042,593 A | 3/2000 | Storz et al. |
| 6,077,230 A | 6/2000 | Gregoire et al. |
| 6,083,177 A | 7/2000 | Kobren et al. |
| 6,086,544 A | 7/2000 | Hibner et al. |
| 6,120,462 A | 9/2000 | Hibner et al. |
| 6,142,946 A | 11/2000 | Hwang et al. |
| 6,213,957 B1 | 4/2001 | Milliman et al. |
| 6,228,055 B1 | 5/2001 | Foerster et al. |
| 6,231,522 B1 | 5/2001 | Voegele et al. |
| 6,273,862 B1 | 8/2001 | Privitera et al. |
| 6,402,701 B1 | 6/2002 | Kaplan et al. |
| 6,409,970 B1 | 6/2002 | Phifer |
| 6,428,486 B2 | 8/2002 | Ritchart et al. |
| 6,436,054 B1 | 8/2002 | Viola et al. |
| 6,485,436 B1 | 11/2002 | Truckai et al. |
| 6,488,636 B2 | 12/2002 | Bryan et al. |
| 6,544,194 B1 | 4/2003 | Kortenbach |
| 6,620,111 B2 | 9/2003 | Stephens et al. |
| 6,626,849 B2 | 9/2003 | Huitema et al. |
| 6,638,235 B2 | 10/2003 | Miller et al. |
| 6,659,338 B1 | 12/2003 | Dittmann et al. |
| 6,758,824 B1 | 7/2004 | Miller |
| 6,849,080 B2 | 2/2005 | Lee et al. |
| 6,986,748 B2 | 1/2006 | McAlister et al. |
| 7,025,098 B2 | 4/2006 | Osborne |
| 7,025,732 B2 | 4/2006 | Thompson et al. |
| 7,185,681 B2 | 3/2007 | Romano |
| 7,189,206 B2 | 3/2007 | Quick et al. |
| 7,204,811 B2 | 4/2007 | Kortenbach et al. |
| 7,226,424 B2 | 6/2007 | Ritchart |
| 7,252,641 B2 | 8/2007 | Thompson et al. |
| 7,276,032 B2 | 10/2007 | Hibner |
| 7,278,991 B2 | 10/2007 | Morris et al. |
| 7,419,472 B2 | 9/2008 | Hibner et al. |
| 7,442,171 B2 | 10/2008 | Stephens et al. |
| 7,445,739 B2 | 11/2008 | Tsonton et al. |
| 7,470,237 B2 | 12/2008 | Beckman et al. |
| 7,497,833 B2 | 3/2009 | Miller |
| 7,556,622 B2 | 7/2009 | Mark et al. |
| 7,575,556 B2 | 8/2009 | Speeg et al. |
| 7,662,109 B2 | 2/2010 | Hibner |
| 7,740,594 B2 | 6/2010 | Hibner |
| 7,740,596 B2 | 6/2010 | Hibner |
| 7,740,597 B2 | 6/2010 | Cicenas et al. |
| 7,749,172 B2 | 7/2010 | Schwindt |
| 7,753,857 B2 | 7/2010 | Hibner |
| 7,758,515 B2 | 7/2010 | Hibner |
| 7,819,819 B2 | 10/2010 | Quick et al. |
| 7,828,745 B2 | 11/2010 | McAlister et al. |
| 7,828,748 B2 | 11/2010 | Hibner |
| 7,854,706 B2 | 12/2010 | Hibner |
| 7,854,707 B2 | 12/2010 | Hibner et al. |
| 7,867,173 B2 | 1/2011 | Hibner et al. |
| 7,896,817 B2 | 3/2011 | Garrison |
| 7,918,804 B2 * | 4/2011 | Monson et al. ............... 600/568 |
| 7,985,239 B2 | 7/2011 | Suzuki |
| 8,016,772 B2 | 9/2011 | Heske et al. |
| 8,038,627 B2 | 10/2011 | Hibner |
| 8,118,755 B2 | 2/2012 | Hibner et al. |
| 8,177,728 B2 | 5/2012 | Hibner et al. |
| 8,177,729 B2 | 5/2012 | Hibner et al. |
| 8,235,913 B2 | 8/2012 | Hibner et al. |
| 8,241,226 B2 | 8/2012 | Hibner et al. |
| 8,262,586 B2 | 9/2012 | Almazan et al. |
| 8,568,335 B2 * | 10/2013 | Monson et al. ............... 600/568 |
| 2002/0076355 A1 | 6/2002 | Phifer |
| 2002/0082518 A1 | 6/2002 | Weiss et al. |
| 2002/0120212 A1 | 8/2002 | Ritchart et al. |
| 2003/0125639 A1 | 7/2003 | Fisher et al. |
| 2003/0199753 A1 | 10/2003 | Hibner |
| 2005/0049521 A1 | 3/2005 | Miller et al. |
| 2005/0065453 A1 | 3/2005 | Shabaz et al. |
| 2005/0165328 A1 | 7/2005 | Heske et al. |
| 2005/0215921 A1 | 9/2005 | Hibner et al. |
| 2005/0215922 A1 | 9/2005 | Tsonton et al. |
| 2006/0041230 A1 | 2/2006 | Davis |
| 2006/0074344 A1 | 4/2006 | Hibner |
| 2006/0074345 A1 | 4/2006 | Hibner |
| 2006/0258955 A1 | 11/2006 | Hoffman et al. |
| 2007/0032741 A1 | 2/2007 | Hibner et al. |
| 2007/0032742 A1 | 2/2007 | Monson |
| 2007/0112751 A1 | 5/2007 | Pyun |
| 2007/0213630 A1 | 9/2007 | Beckman et al. |
| 2007/0239067 A1 | 10/2007 | Hibner et al. |
| 2008/0004545 A1 | 1/2008 | Garrison |
| 2008/0082021 A1 | 4/2008 | Ichikawa et al. |
| 2008/0195066 A1 | 8/2008 | Speeg et al. |
| 2008/0214955 A1 | 9/2008 | Speeg et al. |
| 2010/0075664 A1 | 3/2010 | Maucksch |
| 2010/0106053 A1 | 4/2010 | Videbaek et al. |
| 2010/0152610 A1 | 6/2010 | Parihar et al. |
| 2010/0160816 A1 | 6/2010 | Parihar et al. |
| 2010/0160819 A1 | 6/2010 | Parihar et al. |
| 2010/0160824 A1 | 6/2010 | Parihar et al. |
| 2010/0317997 A1 | 12/2010 | Hibner et al. |
| 2011/0144532 A1 | 6/2011 | Monson et al. |

FOREIGN PATENT DOCUMENTS

| | | |
|---|---|---|
| EP | 1 520 518 | 4/2005 |
| EP | 1 642 533 | 4/2006 |
| EP | 1 832 234 | 12/2007 |
| EP | 1 932 482 | 6/2008 |
| GB | 2 018 601 | 10/1979 |
| RU | 2021770 | 10/1994 |
| WO | WO 03/077768 | 9/2003 |
| WO | WO 2004/016177 | 2/2004 |
| WO | WO 2004/052179 | 6/2004 |
| WO | WO 2004/052212 | 6/2004 |
| WO | WO 2004/075728 | 9/2004 |
| WO | WO 2006/005342 | 1/2006 |
| WO | WO 2006/124489 | 11/2006 |
| WO | WO 2007/019152 | 2/2007 |
| WO | WO 2007/021904 | 2/2007 |
| WO | WO 2007/112751 | 10/2007 |

OTHER PUBLICATIONS

U.S. Appl. No. 60/874,792, filed Dec. 13, 2006, Hibner.
European Search Report dated Dec. 1, 2005 for Application No. EP 05256035.
European Search Report dated Jun. 13, 2007 for Application No. 07250402.
European Search Report dated Nov. 14, 2007 for Application No. 07250926.
European Search Report dated Dec. 11, 2007 for PCT Application No. 07253220.
European Search Report dated Dec. 20, 2007 for EPO Application No. 07253220.
European Examination Report dated May 13, 2008 for Application No. EP 07250402.

(56) References Cited

OTHER PUBLICATIONS

European Examination Report dated Mar. 19, 2009 for Application No. 07250926.
European Search Report dated Apr. 3, 2009 for Application No. 08252518.
European Search Report dated Apr. 3, 2009 for Application No. 08252524.
European Search Report dated Sep. 29, 2010 for Application No. EP 10251076.
European Search Report dated Apr. 5, 2012 for Application No. EP 11193357.
Supplemental European Search Report dated Dec. 16, 2009 for Application No. EP06789155.
European Communication dated Jun. 25, 2007 for Application No. EP 05256035.
Patentability Report and Written Opinion dated Feb. 5, 2008 for Application No. PCT/US2006/030022.
International Search Report dated Jul. 18, 2007 for Application No. PCT/US 06/30022.
International Search Report dated Sep. 27, 2007 for Application No. PCT/US06/30022.
International Search Report dated Dec. 18, 2008 for Application No. PCT/US2008/058627.
Written Opinion dated Apr. 26, 2010 for Application No. EP 08252524.
Non-final Rejection dated Mar. 20, 2008 for U.S. Appl. No. 11/782,963.
Non-final Rejection dated Apr. 4, 2008 for U.S. Appl. No. 11/736,117.
Final Rejection dated Sep. 26, 2008 for U.S. Appl. No. 11/782,963.
Non-Final Rejection dated Oct. 6, 2008 for U.S. Appl. No. 11/736,117.
EnCor MRI Specifications and Breast Biopsy System, SenoRx, 2005, pp. 102.

* cited by examiner

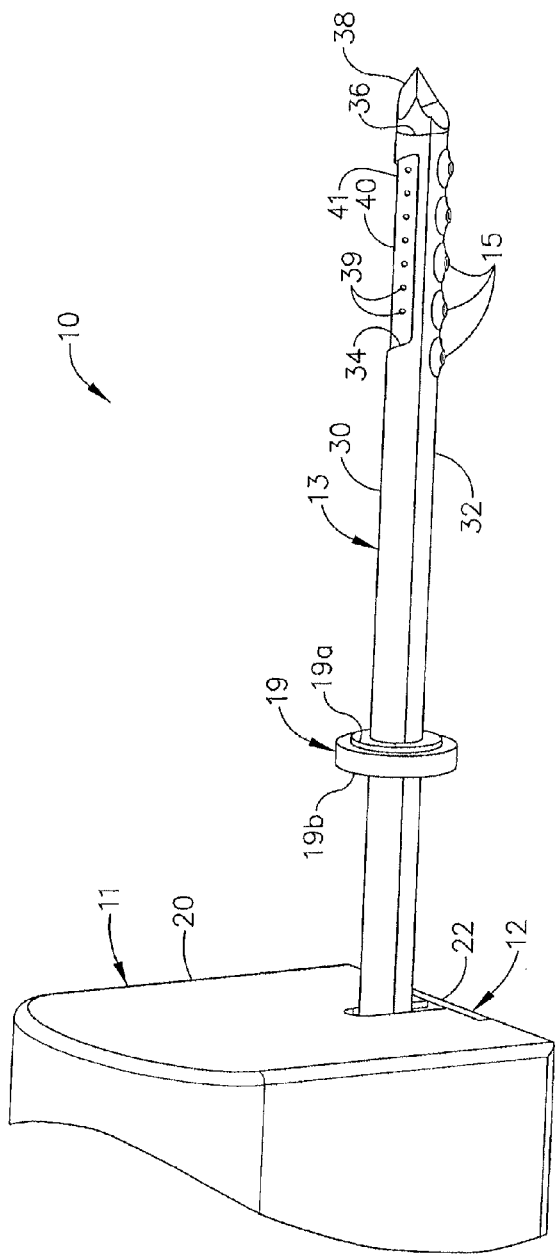
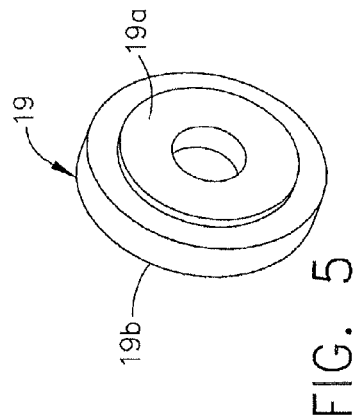
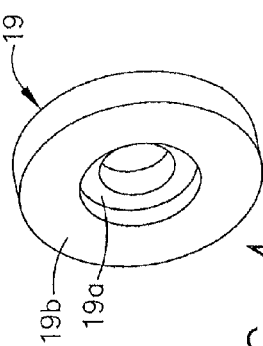

BIOPSY DEVICE WITH VACUUM ASSISTED BLEEDING CONTROL

PRIORITY

The present application is a continuation of U.S. patent application Ser. No. 13/025,366, entitled "Biopsy Device with Vacuum Assisted Bleeding Control," filed Feb. 11, 2011, which is a continuation of U.S. patent application Ser. No. 11/424,576, entitled "Biopsy Device with Vacuum Assisted Bleeding Control," filed Jun. 16, 2006, now U.S. Pat. No. 7,918,804, which is a continuation-in-part of U.S. patent application Ser. No. 11/198,558, entitled "Biopsy Device with Replaceable Probe and Incorporating Vibration Insertion Assist and Static Vacuum Source Sample Stacking Retrieval," filed Aug. 5, 2005, now U.S. Pat. No. 7,867,173, the disclosures of which are hereby incorporated by reference in its entirety.

FIELD OF THE INVENTION

The present invention relates in general to biopsy devices, and more particularly to biopsy devices having a cutter for severing tissue, and even more particularly to biopsy devices for multiple sampling with a probe remaining inserted.

BACKGROUND OF THE INVENTION

When a suspicious tissue mass is discovered in a patient's breast through examination, ultrasound, MRI, X-ray imaging or the like, it is often necessary to perform a biopsy procedure to remove one or more samples of that tissue in order to determine whether the mass contains cancerous cells. A biopsy may be performed using an open or percutaneous method.

An open biopsy is performed by making a large incision in the breast and removing either the entire mass, called an excisional biopsy, or a substantial portion of it, known as an incisional biopsy. An open biopsy is a surgical procedure that is usually done as an outpatient procedure in a hospital or a surgical center, involving both high cost and a high level of trauma to the patient. Open biopsy carries a relatively higher risk of infection and bleeding than does percutaneous biopsy, and the disfigurement that sometimes results from an open biopsy may make it difficult to read future mammograms. Further, the aesthetic considerations of the patient make open biopsy even less appealing due to the risk of disfigurement. Given that a high percentage of biopsies show that the suspicious tissue mass is not cancerous, the downsides of the open biopsy procedure render this method inappropriate in many cases.

Percutaneous biopsy, to the contrary, is much less invasive than open biopsy. Percutaneous biopsy may be performed using fine needle aspiration (FNA) or core needle biopsy. In FNA, a very thin needle is used to withdraw fluid and cells from the suspicious tissue mass. This method has an advantage in that it is very low-pain, so low-pain that local anesthetic is not always used because the application of it may be more painful than the FNA itself. However, a shortcoming of FNA is that only a small number of cells are obtained through the procedure, rendering it relatively less useful in analyzing the suspicious tissue and making an assessment of the progression of the cancer less simple if the sample is found to be malignant.

During a core needle biopsy, a small tissue sample is removed allowing for a pathological assessment of the tissue, including an assessment of the progression of any cancerous cells that are found. The following patent documents disclose various core biopsy devices and are incorporated herein by reference in their entirety: U.S. Pat. No. 6,273,862 issued Aug. 14, 2001; U.S. Pat. No. 6,231,522 issued May 15, 2001; U.S. Pat. No. 6,228,055 issued May 8, 2001; U.S. Pat. No. 6,120,462 issued Sep. 19, 2000; U.S. Pat. No. 6,086,544 issued Jul. 11, 2000; U.S. Pat. No. 6,077,230 issued Jun. 20, 2000; U.S. Pat. No. 6,017,316 issued Jan. 25, 2000; U.S. Pat. No. 6,007,497 issued Dec. 28, 1999; U.S. Pat. No. 5,980,469 issued Nov. 9, 1999; U.S. Pat. No. 5,964,716 issued Oct. 12, 1999; U.S. Pat. No. 5,928,164 issued Jul. 27, 1999; U.S. Pat. No. 5,775,333 issued Jul. 7, 1998; U.S. Pat. No. 5,769,086 issued Jun. 23, 1998; U.S. Pat. No. 5,649,547 issued Jul. 22, 1997; U.S. Pat. No. 5,526,822 issued Jun. 18, 1996; and US Patent Application 2003/0199753 published Oct. 23, 2003 to Hibner et al.

At present, a biopsy instrument marketed under the trade name MAMMOTOME is commercially available from ETHICON ENDO-SURGERY, INC. for use in obtaining breast biopsy samples. These devices generally retrieve multiple core biopsy samples from one insertion into breast tissue with vacuum assistance. In particular, a cutter tube is extended into a probe to cut tissue prolapsed into a side aperture under vacuum assistance and then the cutter tube is fully retracted between cuts to extract the sample.

With a long probe, the rate of sample taking is limited not only by the time required to rotate or reposition the probe but also by the time needed to translate the cutter. As an alternative to this "long stroke" biopsy device, a "short stroke" biopsy device is described in the following commonly assigned U.S. patent application Ser. No. 10/676,944, "Biopsy Instrument with Internal Specimen Collection Mechanism" filed Sep. 30, 2003 in the name of Hibner et al.; and U.S. patent application Ser. No. 10/732,843, "Biopsy Device with Sample Tube" filed Dec. 10, 2003 in the name of Cicenas et al. The cutter is cycled across the side aperture, reducing the sample time. Several alternative specimen collection mechanisms are described that draw samples through the cutter tube, all of which allow for taking multiple samples without removing the probe from the breast.

The vacuum assistance presented at the side aperture provides a further benefit of reducing the accumulation of bodily fluids around the probe that may tend to interfere with taking a diagnostic image, may impede subsequent insufflation and marker deployment, leave an undesirable hematoma at the biopsy site, and/or result in external bleeding that is a biohazard and may increase the patient's discomfort.

While these multiple sample core biopsy instruments have numerous advantages, it is believed that the diagnostic and therapeutic opportunities of core biopsy procedures would be more widely used if bleeding associated with a larger core biopsy probe were controlled and/or reduced.

SUMMARY OF THE INVENTION

The present invention addresses these and other problems of the prior art by providing a biopsy device and method that has a probe that is inserted into tissue to obtain a core biopsy sample by translating a cutter with the probe. Bleeding and fluid management is facilitated by a plurality of external holes in the probe that communicate through the probe tube to a vacuum supply. Thereby hematomas or external bleeding from around the probe, that would otherwise degrade diagnostic imaging or present other complications, is mitigated.

In one aspect of the invention, a biopsy device hand piece has a motorized translation and rotation drive mechanism that engages and operates a disposable probe assembly that includes the probe tube with the plurality of external holes. A cutter tube acts as the cutter translating with the probe tube, severing tissue that is prolapsed into the probe tube also under the urging from the vacuum supply.

In another aspect of the invention, a hemostatic ring pad is engageable to the probe tube to contact the skin during the biopsy procedure around an insertion point to reduce external bleeding.

These and other objects and advantages of the present invention shall be made apparent from the accompanying drawings and the description thereof.

BRIEF DESCRIPTION OF THE DRAWINGS

While the specification concludes with claims particularly pointing out and distinctly claiming the present invention, it is believed the same will be better understood by reference to the following description, taken in conjunction with the accompanying drawings in which:

FIG. 3 is an isometric right-side detail view of a distal portion of the biopsy device of FIG. 1 with the disposable probe assembly mounted to the reusable hand piece and having a probe with a piercing tip rotatably attached to a probe tube.

FIG. 4 is a front isometric view of the hemostatic ring pad of FIG. 1.

FIG. 5 is a back isometric view of the hemostatic ring pad of FIG. 1.

DETAILED DESCRIPTION OF THE INVENTION

Figure 1:
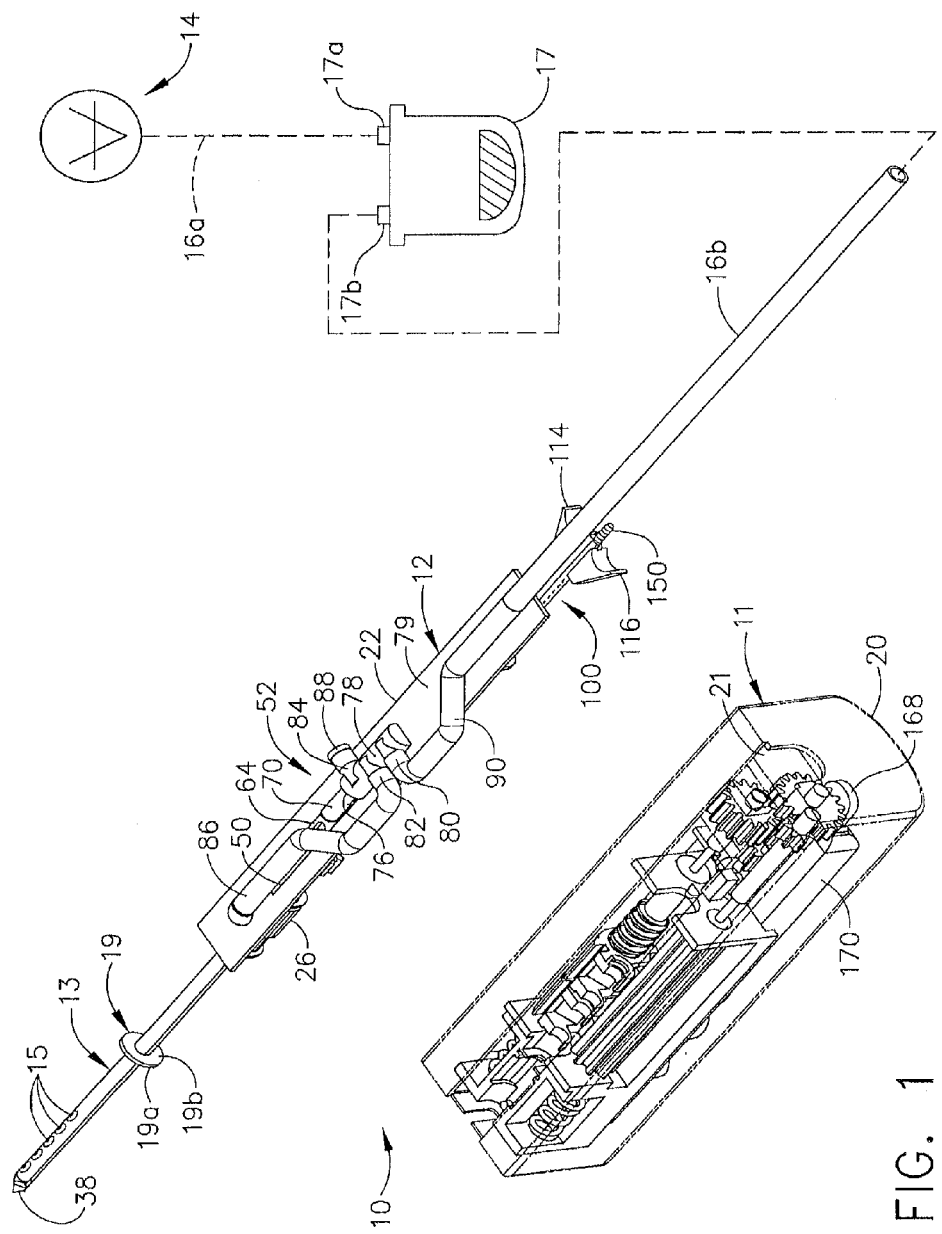
FIG. 1 is an isometric, inverted view of a biopsy device including a disposable probe assembly incorporating bleeding fluid management and including a detached reusable hand piece with a housing depicted in phantom and diagrammatically attached to a vacuum canister and vacuum supply.
Figure 2:
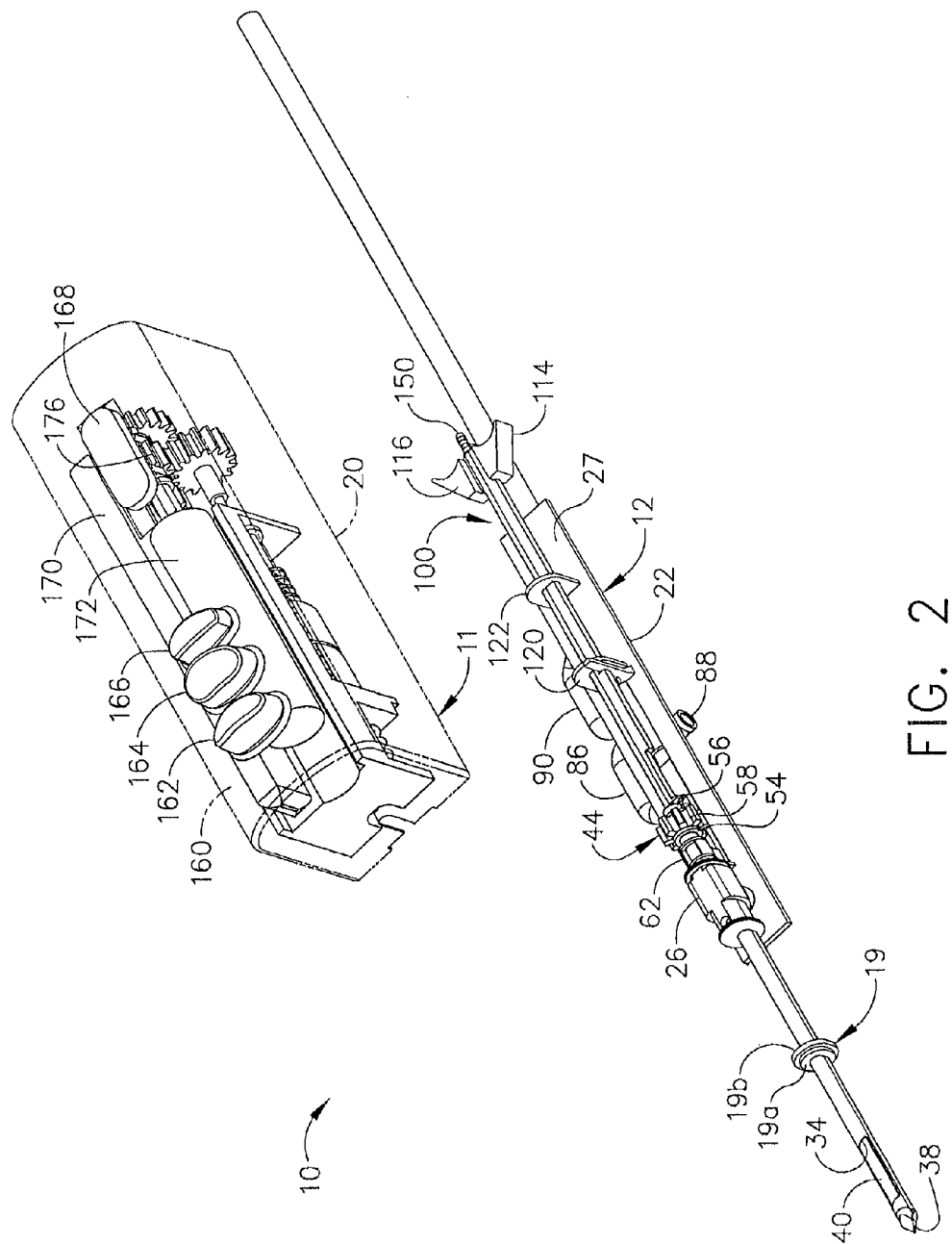
FIG. 2 is an isometric view of the biopsy device of FIG. 1.
Figure 6:
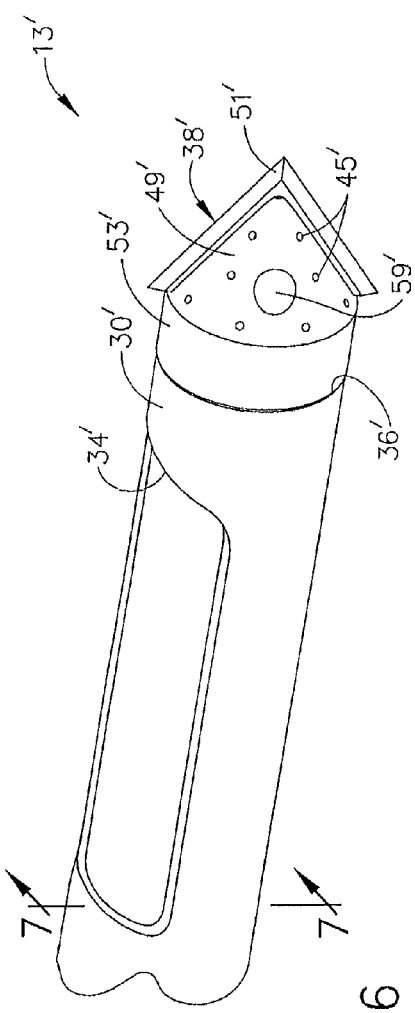
FIG. 6 is a right isometric view of a distal portion of an alternate cylindrical probe with a "soft-walled" vacuum lumen formed by an off-center cutter tube and a freely rotating piercing tip for the biopsy device of FIG. 1.

In FIGS. 1-2, a biopsy device 10 has a reusable hand piece 11 and a disposable probe assembly 12 that enables economical taking of multiple percutaneous core biopsy samples through a core biopsy needle (probe) 13 that is inserted into tissue. With particular reference to FIG. 1, vacuum assisted multiple tissue sample biopsy and retrieval is enabled by a vacuum source 14 (e.g., standard medical vacuum pump or wall-mounted vacuum access port). Advantageously, bleeding and fluid management is enhanced by drawing fluid through external vacuum holes 15 formed distally in the probe 13 of the disposable probe assembly 12 through a first interfacing vacuum conduit 16a which connects the vacuum source 14 to a first port 17a of a vacuum canister 18 for catching extracted fluids and a second interfacing vacuum conduit 16b which connects a second port 17b of the vacuum canister 18 to the disposable probe assembly 12.

In FIGS. 3-5, bleeding and fluid management is further enhanced by proximally positioning a disk-shaped hemostatic ring pad 19 over the probe 13 positioned away from a housing 20 of the reusable hand piece 11 to abut an external opening formed through the skin (not shown). A front absorbent surface 19a of the hemostatic ring pad 19 absorbs fluid and resiliently contacts the skin. An opaque and impermeable back surface (e.g., dark thermoplastic) 19b of the hemostatic ring pad 19 supports the front absorbent surface 19a, obscures patient view of absorbed blood, and completes a pneumatic seal over the opening. The hemostatic ring pad 19 may frictionally engage the probe 13. In order to accommodate a range of sizes of probes 13, a through hole may be formed by inserting the probe 13 through the hemostatic ring pad 19. For instance, the sterility of the absorbent material may be maintained by packing that is adhesively attached to a front outer ring of the back surface 19b. The remaining adhesive may facilitate placement of the hemostatic ring pad at a desired insertion point on the skin a scored central portion of the hemostatic ring pad 19 helps locate the insertion point of the probe 13.

It should be appreciated that although the illustrative version is disk-shaped, it a hemostatic pad consistent with aspects of the present invention may have various geometric shapes. In addition, the absorbent material may be omitted relying upon compression asserted by the back surface. Alternatively, the backing may be omitted relying solely upon absorption or the inherent stiffness of the absorbent material. Further, in some applications it may be desired not to use an opaque backing material but rather a translucent or transparent material so as to view the amount of external bleeding. As an alternative to the hemostatic ring pad 19 frictionally engaging the probe 13, locking features may be incorporated between a hemostatic ring pad and a probe to locking the hemostatic ring pad at a proximal position indicating full insertion.

Returning to FIGS. 1-2, in the illustrative version, the hand piece 11 is self-powered and suitable for use in conjunction with ultrasonic diagnostic imaging. The disposable probe assembly 12 reduces the portion of biopsy device 10 that requires protective packaging to avoid contact with sharp surfaces and to keep it sterile prior to use. Further economy is accomplished by reducing the portion of the biopsy device 10 that is disposed as medical waste between uses. Movable components of the disposable probe assembly 12 are advantageously locked until mounted in an access trough 21 (FIG. 1) formed in the housing 20 of the reusable hand piece 11. It should be appreciated that one or more standard mechanical, pneumatic, or electrical latches (not shown) may be integrated into the biopsy device 10 to secure the disposable probe assembly 12 to the reusable hand piece 11.

Figure 10:
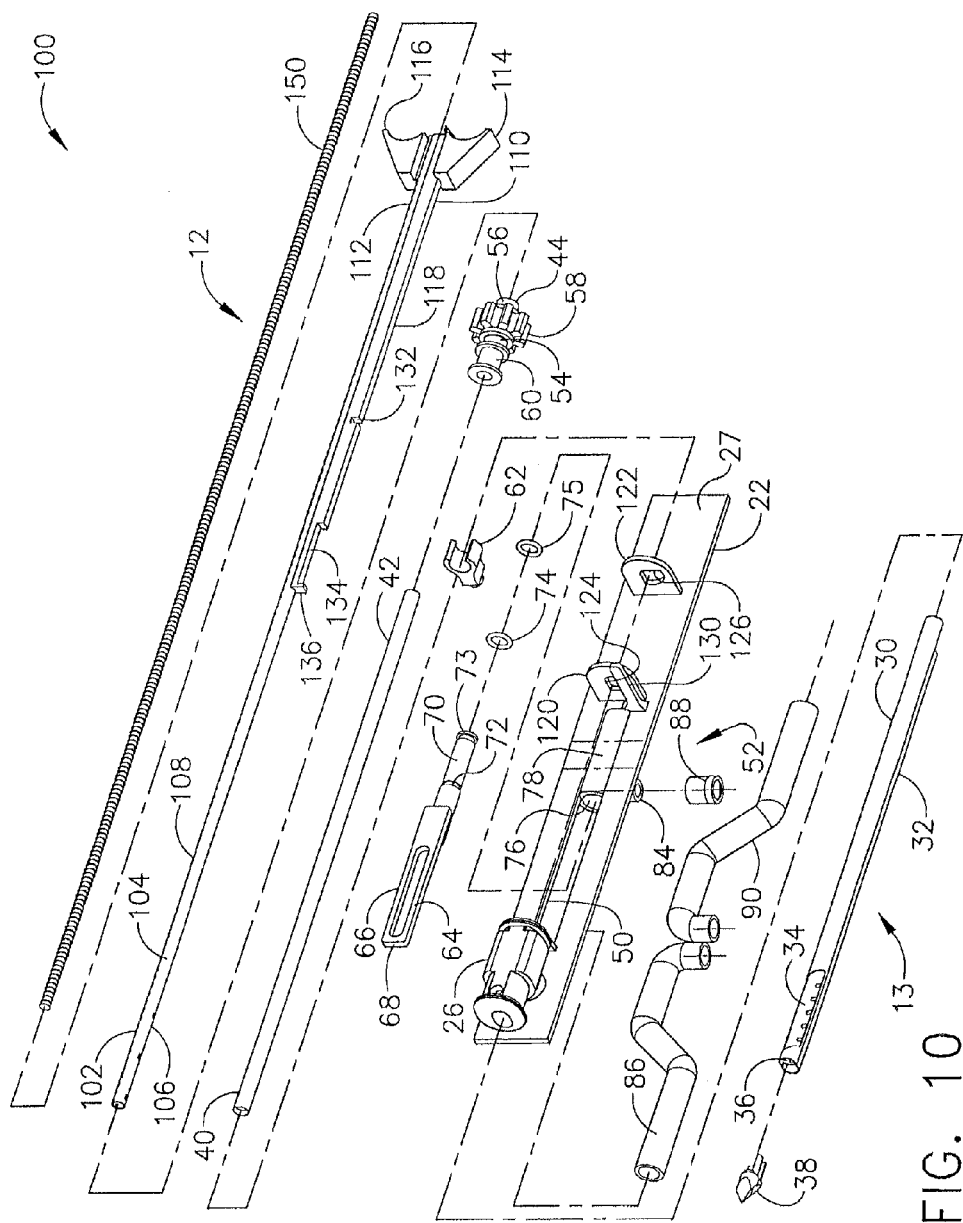
FIG. 10 is an isometric exploded view of the disposable probe assembly of FIG. 1.

In FIGS. 1-3 and 10-11, the disposable probe assembly 12 includes a substantially rectangular cover 22 sized to close the access trough recess 21 (FIG. 1). An end slot 24 formed in the housing 20 is closed by a probe union sleeve 26 attached to an inner surface 27 of the substantially rectangular cover 22. The core biopsy needle ("probe") assembly 13 passes longitudinally through the probe union sleeve 26 and is formed by a probe tube 30 with underlying vacuum lumen 32 that communicates with a side aperture 34 through inter lumen holes 35 (FIG. 11) near a distal opening 36 of the probe tube 30 that is closed by a piercing tip 38. A cutter tube 40 is sized to closely fit and translate within an inner diameter (i.e., cutter lumen) of the probe tube 30. Cutter holes 39 near a distal end 41 of the cutter tube 40 may be included allow bleeding and fluid management through the cutter tube 40. The cutter tube 40 has a longitudinal length sufficient to close the side aperture 34 with a proximal end 42 extending from the probe union sleeve 26 to attach to a cutter gear 44, as depicted in FIGS. 2, 10. This non-cylindrical probe 13 includes one passage that passes through the cutter tube 40 that is encompassed closely by the probe tube 30 and includes a "hard-walled" vacuum (lateral) lumen 32 that is under slung and attached to the probe tube 30, communicating with the other passage proximate to the side aperture 34.

Figure 7:
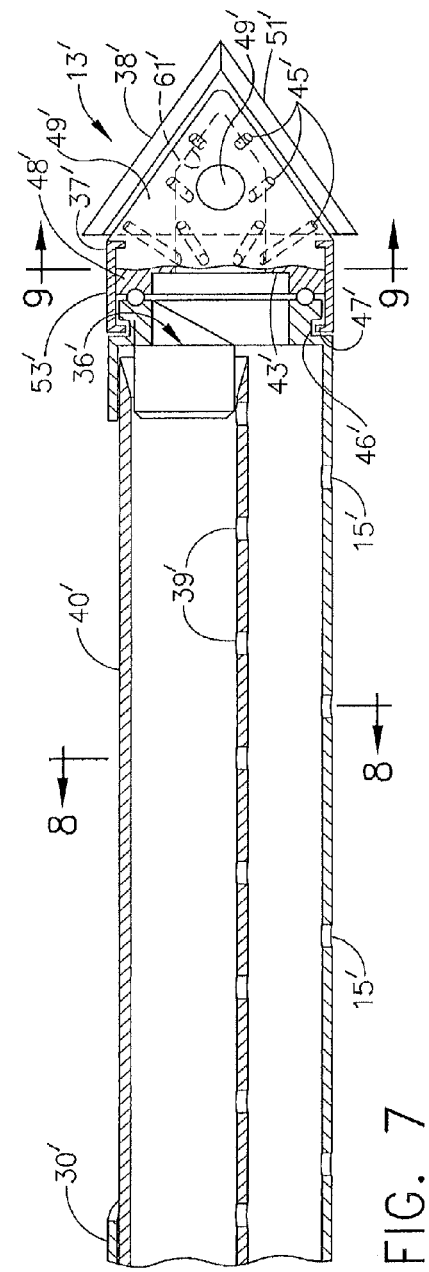
FIG. 7 is a right side view in longitudinal vertical cross section through lines 7-7 of the alternate cylindrical probe of FIG. 6.
Figure 8:
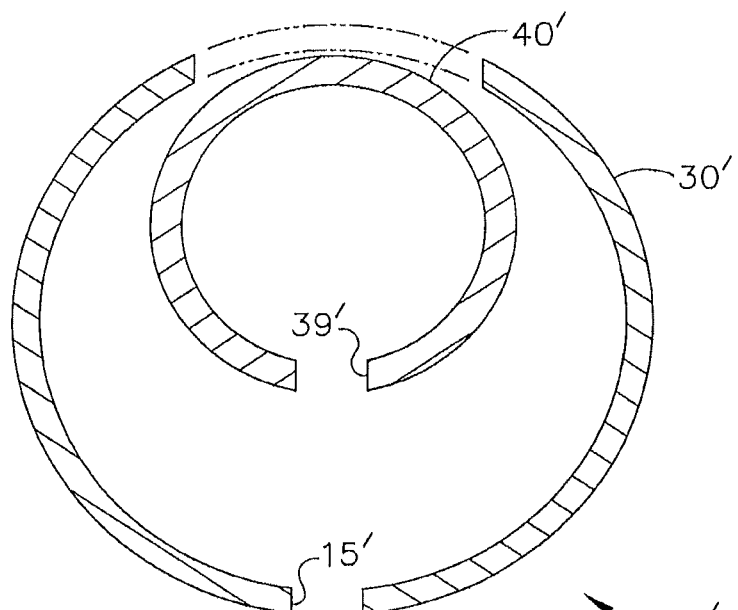
FIG. 8 is a front view taken in transverse cross section along lines 8-8 of the probe of FIG. 7.
Figure 9:
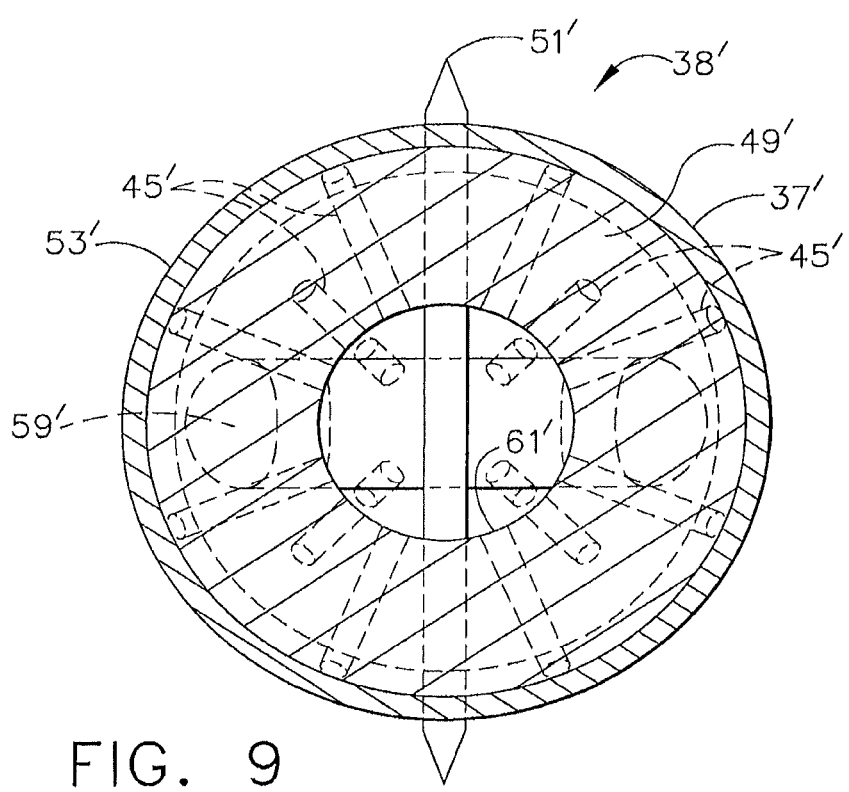
FIG. 9 is an aft view taken in transverse cross section along lines 9-9 of the probe of FIG. 7.

In FIGS. 6-9, an alternate cylindrical probe 13' for the disposable probe assembly 12 of FIG. 1 advantageously incorporates a piercing tip 38' attached at a proximal circular external recess 37' (FIG. 7) for free rotation about its longitudinal axis to a distal opening in a probe tube 30'. Thereby, desired non-conical cutting surfaces may be incorporated that reduce the insertion forces that do not impede rotation of the probe tube 30'. With particular reference to FIG. 7, the cylindrical distal end of the probe tube 30' ends in an outer race 46' proximal to a recessed lip 47'. The piercing tip 38' is formed by a cylindrical base 48' attached to a split cone tip 49' that receives a triangular blade 51' held by beveled pin 59'. A cylindrical collar 53' grips the cylindrical base 48' and has proximal inward lip 55' that resides within the outer race 46' of the probe tube 30'. A bearing 57' between the recessed lip 47' of the probe tube 30' and the cylindrical base 48' of the piercing tip 38' enhances low friction rotation. Thus, a cutting surface such as the triangular blade 51' may be selected for reduced insertion force, etc., yet not impede rotation of the side aperture 34' of the probe tube 30'.

In this illustrative version, an axially off-center cutter tube 40' (FIGS. 7-8) within the probe tube 30' acts as a "soft-wall", defining first and second fluid passages that are separated longitudinally within the probe tube 30' that distally communicate with each other at a side aperture 34' formed in the probe tube 30'. A first fluid passage is defined within the cutter tube 40' and the second fluid passage is defined within the probe tube 30' but outside of cutter tube 40'. Fluid communication between the fluid passages is enhanced by a concave proximal end 43' of piercing tip 38' and cutter holes 39'.

Bleeding and fluid management is also enhanced by a central fluid cavity 61' that communicates between the distal opening 36' of the probe tube 30' and small fluid passages 45' formed in the split cone tip 49' of the piercing tip 38' that transition from the concave proximal end 43' to an exterior of the piercing tip 38'.

With particular reference to FIG. 10, proximal to the probe union sleeve 26 is an elongate slot 50 that is part of a vacuum assist valve assembly 52. The cutter gear 44 includes distal and proximal annular recesses 54, 56 flanking spur gear teeth 58 that engage the reusable hand piece 11 as described below. A more distal annular recess 60 is gripped by a post 62 that is engaged to longitudinally translate in an elongate post slot 64 of a distal portion 66 of a vacuum valve actuator 68. A cylindrical proximal portion 70 of the vacuum valve actuator 68 has distal and proximal O-ring grooves 72, 73 that respectively retain distal and proximal dynamic O-ring seals 74, 75 that move within a distally open cylindrical valve bore 76 of a valve body 78 molded onto an outer surface 79 of the substantially rectangular cover 22 (FIG. 1).

With particular reference to FIG. 1, as described and depicted in the cross referenced patent application Ser. No. 11/198,558 incorporated by reference above, the vacuum valve actuator 68 selectively allows communication between a proximal port 80, a center port 82, and a distal port 84 (FIG. 2). In particular, with the cutter gear 44 retracted, the proximal and center ports 80, 82 are in communication. With the cutter gear translated distally, the center and distal ports 82, 84 communicate. The center port 82 is attached to a distal vacuum conduit 86 whose other end is connected through the rectangular cover 22 to the probe union sleeve 26. It should be appreciated that the probe union sleeve 26 includes pneumatic passages that communicate between a proximal end of the vacuum lumen 32 and the distal vacuum conduit 86. The distal port 84 is attached to a hose nib 88 that is exposed to atmospheric pressure. Hose nib 88 may include an air and/or saline filter. Alternatively, hose nib 88 may be connected to a positive pressure source (e.g., fluid pump) or a negative pressure source (e.g., vacuum pump, syringe) to aspirate fluids. Likewise, hose nib 88 may be used to lavage the tissue cavity with saline, pain medication, or bleeding control fluids. The proximal port 80 communicates through a proximal vacuum conduit 90 to the interfacing vacuum conduit 16a.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

With further reference to FIGS. 2-3 and 10-11, a sample extraction feature is incorporated so that multiple samples may be made without the need to remove the probe 13 from tissue nor even to full retract the cutter tube 40 to retract a tissue specimen to the reusable hand piece 11. With particular reference to FIG. 10, this feature is accomplished with a stacking straw assembly 100. An elongate straw 102 is scored down its length on opposite sides by grooves 104 defining first and second straw halves 106, 108, whose respective proximal, outer surfaces 110, 112 are attached to triangular grips 114, 116, respectively. A locking strip 118 extends distally from one triangular grip 114 and is attached along a proximal portion of the first straw half 106.

Figure 11:
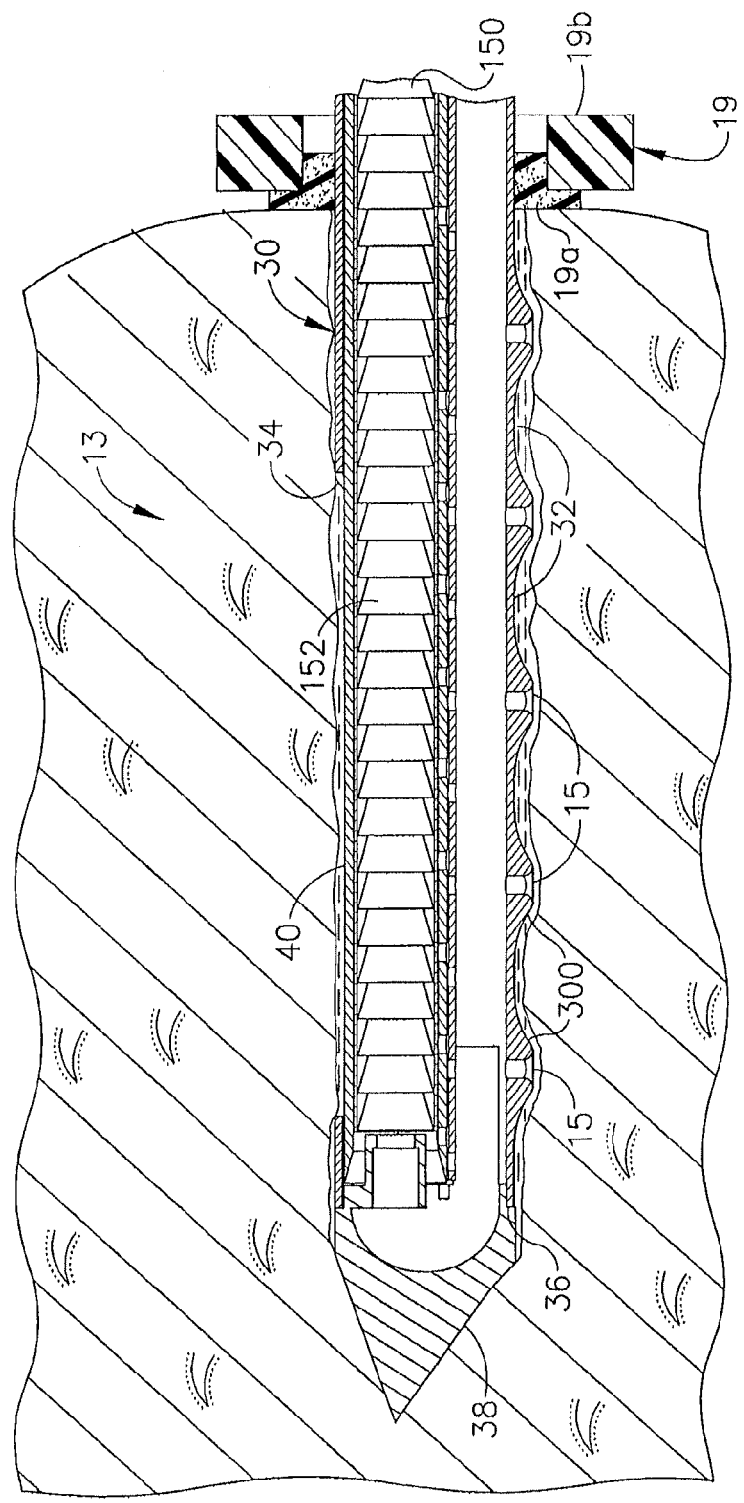
FIG. 11 is a left side view in elevation taken in longitudinal cross section through a probe for the disposable probe assembly of FIG. 1 inserted into tissue.
Figure 12:
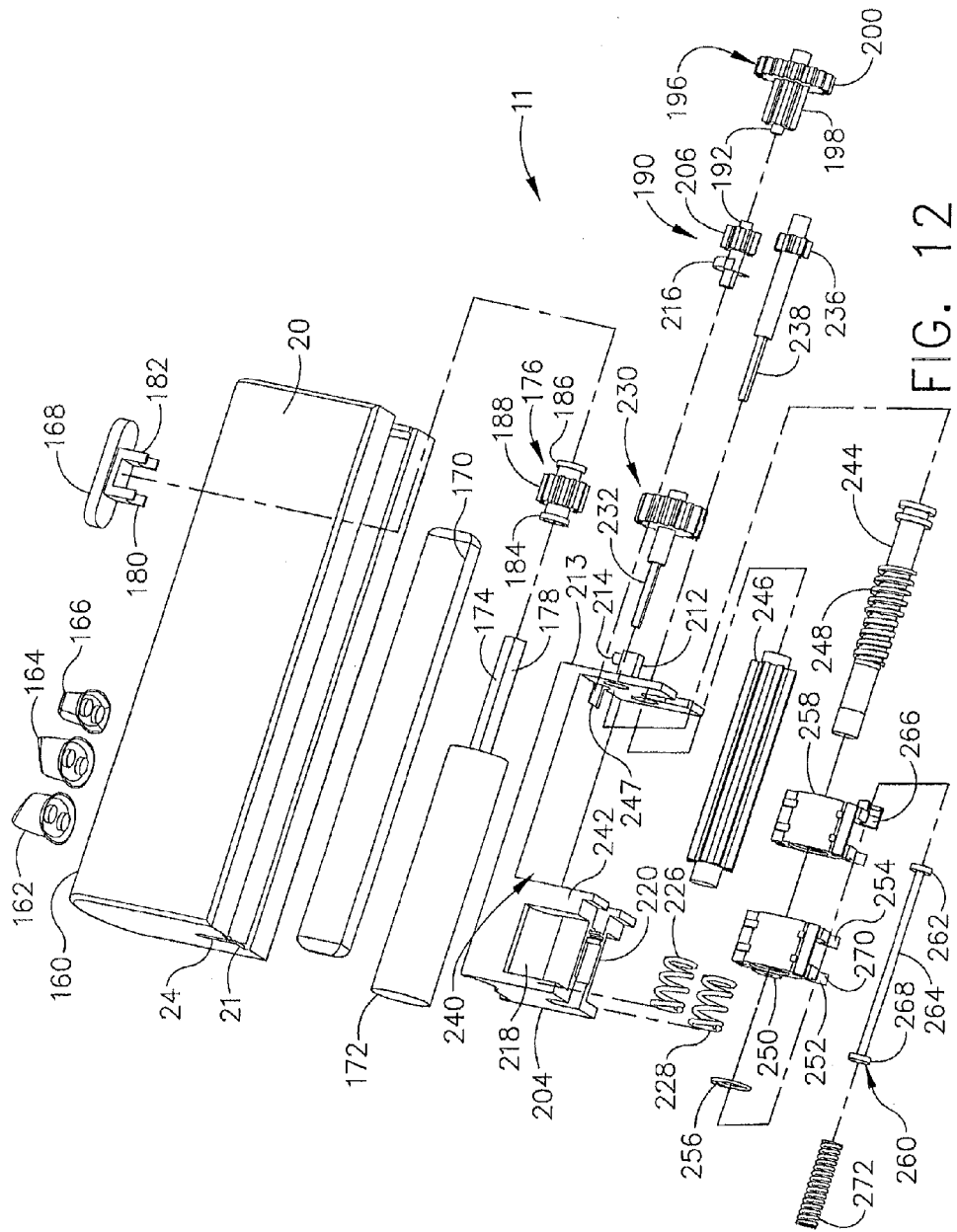
FIG. 12 is an isometric exploded view of the reusable hand piece of FIG. 1.

Distal and proximal tabs 120, 122 extend from the inner surface 27 of the substantially rectangular cover 22, each having a respective through hole 124, 126 through which the stacking straw assembly 100 is inserted. The through holes 124, 126 are shaped to allow the locking strip 118 to rotate ninety (90) degrees. A bayonet locking member 130 also extends from the inner surface 27 of the substantially rectangular cover 22 just distal and laterally offset from the through hole 124 of the distal tab 120 to lock into an alignment locking slot 132 in the locking strip 118 when laterally rotated. The bayonet locking member 130 prevents axial movement of the stacking straw assembly 100. The cutter gear 44 and cutter tube 40 cannot move proximally due to contact with the stacking straw assembly 100 and cannot move distally due to contact with the probe union sleeve 26. By securing both the cutter gear 44 and the stacking straw assembly 100 in a full distal axial position, the disposable probe assembly 12 is aligned to engage the components of the reusable hand piece 11 as described below. Distal to the alignment locking slot 132, a rectangular recess 134, formed in the locking strip 118, defines a distal-most locking finger 136 for engaging components of the reusable hand piece 11 that positions the stacking straw assembly 100 as described below. In FIGS. 10-11, an indicator tube 150 has a stacked cone-shaped outer surface 152 (FIG. 11) that slides within the elongate straw 104 that in turn slides within the cutter tube 40.

An alternative sample retrieval approach ("proximal stacker") is also described in the aforementioned patent application Ser. No. 11/198,558 that uses vacuum without a stacking straw 104 (not shown). In addition, a similar sample holding portion that does not use a stacking straw 104 for retrieval is described in five commonly-owned and co-pending U.S. patent application Ser. No. 10/953,834, "Biopsy Apparatus and Method", END-5469; Ser. No. 10/953,904, "Improved Biopsy Apparatus and Method", END 5470; Ser. No. 10/953,397, "Fluid Control for Biopsy Device", END 5471; Ser. No. 10/953,395, "Biopsy Device with Sample Storage", END 5472; and Ser. No. 10/953,389, "Cutter for Biopsy Device", END 5473, all to Hibner et al. and filed on 29 Sep. 2004, the disclosures of which are hereby incorporated by reference in their entirety.

It should be appreciated that with the benefit of the present disclosure, various configurations of internal and external vacuum holes may be incorporated into a probe consistent with aspects of the invention in order to achieve tissue prolapse, sample retrieval, and bleeding and fluid management. It should also be appreciated that the probe 13 defines first and second fluid passages that are separated longitudinally within the probe 13 and distally communicate with each other at the side aperture 34. In the illustrative version, the first fluid passage is defined within the cutter tube 40 and the second fluid passage is defined within the lateral lumen 32 that is "hard walled" apart from a cylindrical portion of the cutter lumen of the probe tube 35. However, for a cylindrical probe tube (not shown), a cutter tube may be axially offset within the cutter lumen of the probe tube such that the cutter tube may separate the first and second fluid passages, especially if the cutter tube need not be retracted for retraction of samples (e.g., vacuum retraction, straw retraction, single sample per insertion devices).

Figure 13:
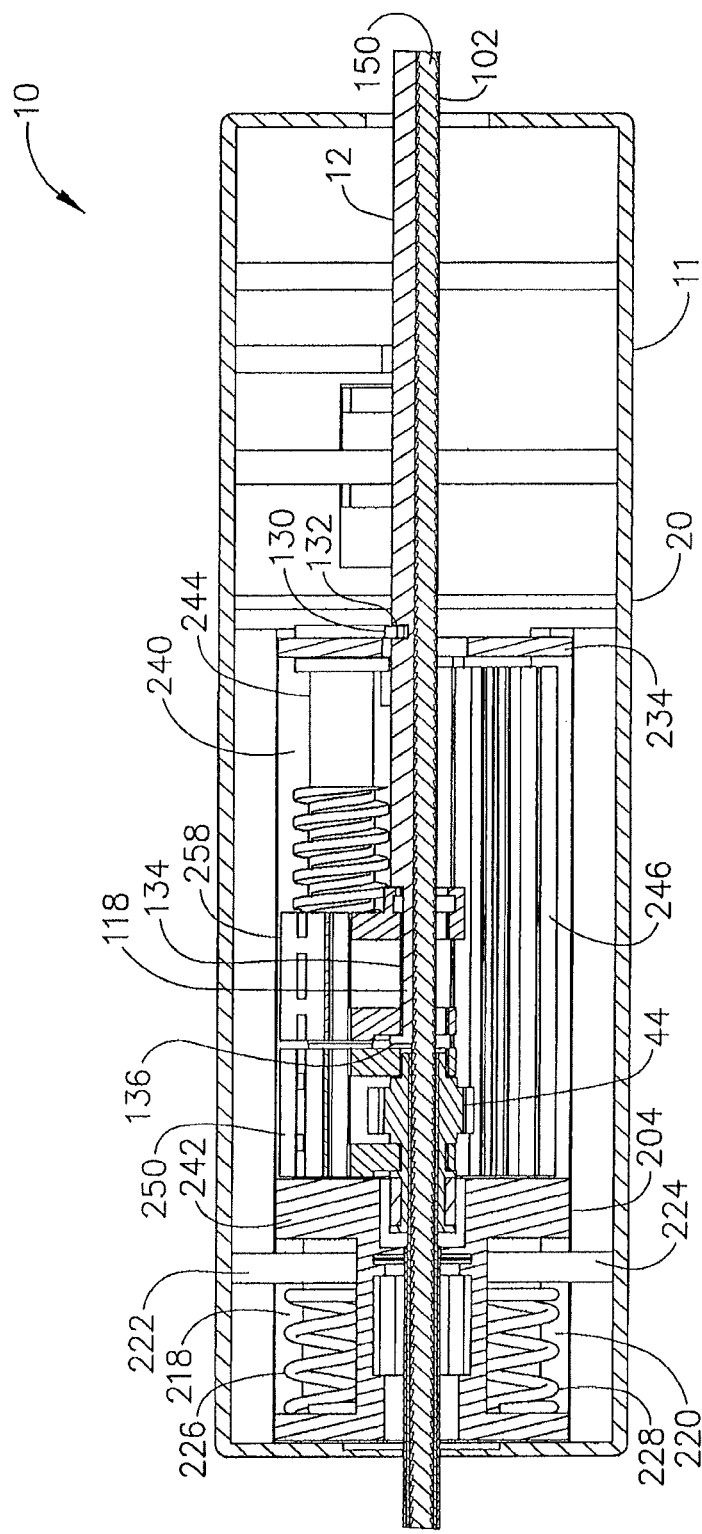
FIG. 13 is a bottom view of the assembled biopsy device of FIG. 1 taken in horizontal cross section through the probe.
Figure 14:
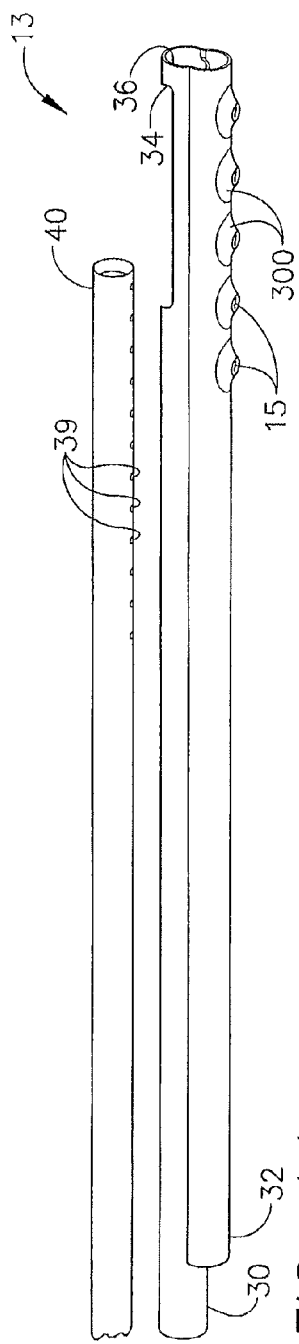
FIG. 14 is an isometric view of the probe having dimpled external vacuum holes formed on the disposable probe assembly of FIG. 1 with a piercing tip omitted and a cutter tube detached.
Figure 15:
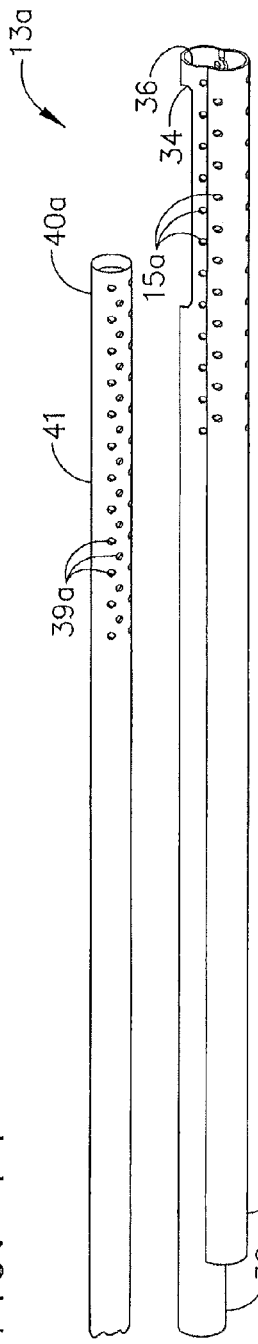
FIG. 15 is an isometric view of an alternate probe having a plurality of longitudinal rows of external vacuum holes for the disposable probe assembly of FIG. 1 with a piercing tip omitted and a cutter tube detached also having a plurality of longitudinal rows of holes.

With reference to FIGS. 1-2, 13-15, the reusable hand piece 11, as described in previously cross referenced U.S. patent application Ser. No. 11/198,558, includes four user controls aligned on a top surface 160 of the housing 20, specifically from most distal to most proximal: a forward motor rotation key 162, a reverse motor rotation key 164, a saline flush key 166 and a slide button 168 for selecting insertion mode or sample taking mode. The keys 162-166 control a control circuit 170, which may include integral power storage (e.g., batteries, fuel cell, etc.) for untethered use. With particular reference to FIG. 15, the forward motor rotation key 162 causes a DC motor 172 to rotate its motor output shaft 174 in a forward rotation. A slide spur gear 176 includes an internal keyed engagement with a longitudinal key groove 178 on the motor output shaft 174 that allows longitudinal positioning by the slide button 168. In particular, fore and aft brackets 180, 182 of the slide button 168 engage distal and aft annular grooves 184, 186 that flank spur gear teeth 188 of the slide spur gear 176.

When the slide button 168 is moved distally, the slide spur gear 176 engages a tissue penetration gear 190 that spins on a common shaft centerline 192 forward of a gearbox input gear 196. Gearbox input gear 196 consists of a distal small gear 198 and a proximal large gear 200. The tissue penetration gear 190 has spur gear teeth 206 that engage the slide spur gear 176. A frame post 212 projects proximally from an aft wall 213 of a frame 204 with a strike pin 214 projecting upwardly from the frame post 212. A circular cam wheel 216 is attached to a distal side of the tissue penetration gear 190. Rotating the tissue penetration gear 190 urges the strike pin 214, and thus the frame 204, proximally. Left and right spring cavities 218, 220 (when viewed from above), formed longitudinally in distal corners of the frame 204, respectively receive inwardly projecting left and right tabs 222, 224 (FIG. 1) from the housing 20 and receive left and right compression springs 226, 228. In particular, a distal end of each compression spring 226, 228 presses against a distal inner surface of the respective spring cavity 218, 220. A proximal end of each compression spring 226, 288 is grounded against a respective tab of the housing 20. Thus, the frame 204 is biased distally within the housing 20. Movement of the frame 204 proximally compresses these compression springs 226, 228 that thereafter assert a restoring force.

When the slide button 168 is moved proximally, the slide spear gear 176 is moved into engagement with the gearbox input gear 196, specifically the distal small gear 198, which engages and turns a translation large input gear 230 whose shaft 232 passes through the aft wall 213 of the frame 204. The proximal large gear 200 of the gearbox input gear 196 engages and turns a rotation small input gear 236 whose shaft 238 passes through the aft wall 213. The frame 204 includes a carriage recess 240, defined between a partition 242 and the aft wall 213. The carriage recess 240 contains longitudinally aligned left side lead (translation) screw 244 and right-side rotation spur gear 246 that are attached for rotation respectively with the shafts 232, 238. The partition 242 is positioned aft of the left and right tabs 222, 224 of the housing 20 and also defines in part the left and right spring cavities 218, 220. An unlocking cam 247 projects proximally from and is longitudinally centered on the aft wall 234 above the position of the lead (translation) screw 244 and rotation spur gear 246.

The rotation spur gear 246 engages the cutter gear 44 when the disposable probe assembly 12 is inserted, imparting a rotation as the cutter tube 40 and cutter gear 44 translate longitudinally in response to the rotation of the lead (translation) screw 244. This translation is caused by lead screw threads 248. In particular, a distal carriage (cutter carriage) 250 is longitudinally moved on the lead screw threads 248. Distal and proximal J-hook extensions 252, 254 project downwardly from the distal carriage 250 to engage the distal and proximal annular recesses 54, 56 of the cutter gear 44. Distal of the distal carriage 250, a biasing spring 256 urges against the distal carriage 250, which assists in engagement of the lead screw threads 248 with the distal carriage 250.

A sliding pin 260 has a proximal carriage sliding pin retainer 266 attached to a proximal carriage 258. A shaft 264 of the sliding pin 260 also passes through a distal carriage sliding pin retainer 270 attached to the distal carriage 250. Sliding pin 260 has a proximal end 262 and a distal end 268 to prevent the sliding pin 260 from disengaging from the carriage sliding pin retainers 266, 270. A sliding pin spring 272 resides on the sliding pin 260 and is constrained at each end by carriage sliding pin retainers 266, 270.

With the components of FIGS. 1-5 and 10-13 now introduced, a sequence of use of the biopsy device 10 will be described. The interfacing vacuum lumen 16a is attached to the disposable probe assembly 12 (FIGS. 1-2). The disposable probe assembly 12 is installed into the reusable hand piece 11 (FIGS. 3, 13). In so doing, the distal cutter carriage 250 engages the cutter gear 44, the proximal straw carriage 258 engages the locking strip 118 of the stacking straw assembly 100, and the bayonet locking member 130 is deflected by the unlocking cam 247, longitudinally unlocking from the alignment locking slot 132 of the locking strip 118 allowing longitudinal movement of the cutter tube 40 and the straw stacking assembly 100.

With the biopsy device 10 assembled, the reusable handpiece 11 is manipulated to insert the piercing tip 38 of the core biopsy needle (probe) assembly 13 into tissue. Penetration of dense tissue is assisted by moving the slide button 168 distally to a "tissue insertion mode" wherein the slide spur gear 176 engages the tissue penetration gear 190. Depression of the forward motor rotation key 162 turns these gears 176, 190 causing the circular cam wheel 216 to turn against strike pin 214 that creates proximal longitudinal motion of frame 204 and the attached core biopsy needle (probe) assembly 13 of approximately 0.1 inch at a rotation rate of 7 cycles per second. Left and right compression springs 226, 228 provide the restoring distal longitudinal motion to frame 204 and probe assembly 28 as left and right compression springs 226, 228 are repeatedly compressed between the distal surface of the left and right spring cavities 218, 220 of the frame 204 and the left and right tabs 222, 224 of the housing 20. The restoring distal longitudinal motion to frame 204 and core biopsy needle (probe) assembly 28 result in a corresponding distal motion of piecing tip 38 that assists in penetrating tissue.

Bleeding and fluid management is enhanced by vacuum being drawn through the external vacuum holes 15 into the vacuum lumen 32. With reference to FIGS. 11 and 14, the external vacuum holes 15 reside within a protruding dimple structure 300 formed in the lateral lumen 32 which mitigates a tendency of adjacent tissue to be drawn into and plug an external vacuum hole 15. In addition, the cutter holes 39 formed in a distal end 41 of the cutter tube 40 assist in drawing fluid when the cutter tube 40 is advanced, otherwise closing the side aperture 34.

In FIG. 15, an alternate probe 13a has a plurality of longitudinal rows of external vacuum holes 15a. A cutter tube 40a has a plurality of longitudinal rows of cutter holes 39a for assisting in bleeding and fluid management. In addition, the exterior of a probe tube 30a has some of the vacuum holes 15a, in addition to those in a vacuum lumen 32a, such that cutter holes 39a in the cutter tube 40a may readily communicate externally.

Figure 16:
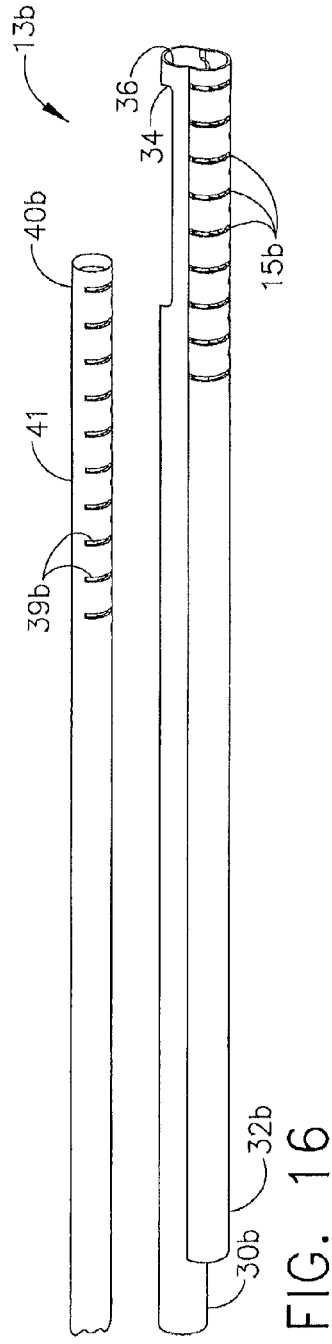
FIG. 16 is an isometric view of another alternate probe having a longitudinally spaced plurality of transverse external vacuum slots for the disposable probe assembly of FIG. 1 with a piercing tip omitted and a cutter tube detached also having a plurality of longitudinally spaced plurality of transverse holes.

In FIG. 16, another alternate probe 13b has a longitudinally spaced plurality of transverse external vacuum slots 15b formed in a vacuum lumen 32b but not a probe tube 30b. A cutter tube 40b also has a plurality of longitudinally spaced plurality of transverse cutter slots 39b.

Figure 17:
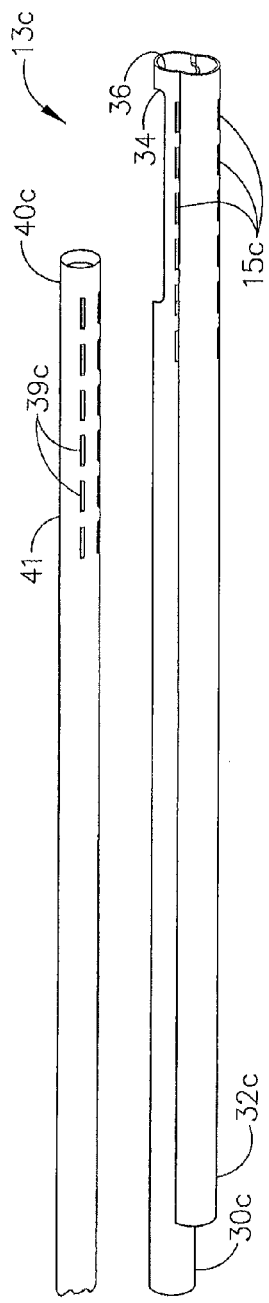
FIG. 17 is an isometric view of an additional alternate probe having a plurality of longitudinal external vacuum slots aligned into radially spaced longitudinal rows for the disposable probe assembly of FIG. 1 with a piercing tip omitted and a cutter tube detached also having a plurality of longitudinal slots.

In FIG. 17, an additional alternate probe 13c has a plurality of longitudinal external vacuum slots 15c formed in both a vacuum lumen 32c and a probe tube 30c. A cutter tube 40c also has a plurality of longitudinal cutter slots 39c.

Figure 18:
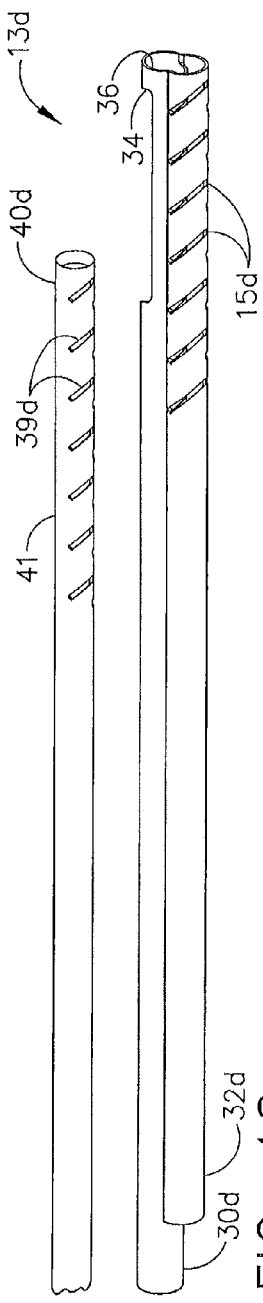
FIG. 18 is an isometric view of a further alternate probe having a plurality of parallel, spiraled external vacuum slots for the disposable probe assembly of FIG. 1 with a piercing tip omitted and a cutter tube detached also having a plurality of spiraled slots.

In FIG. 18, a further alternate probe 13d has a plurality of parallel, spiraled external vacuum slots 15d formed in a vacuum lumen 32d but not a probe tube 30d. A cutter tube 40d also has a plurality of spiraled cutter slots 39d.

Figure 19:
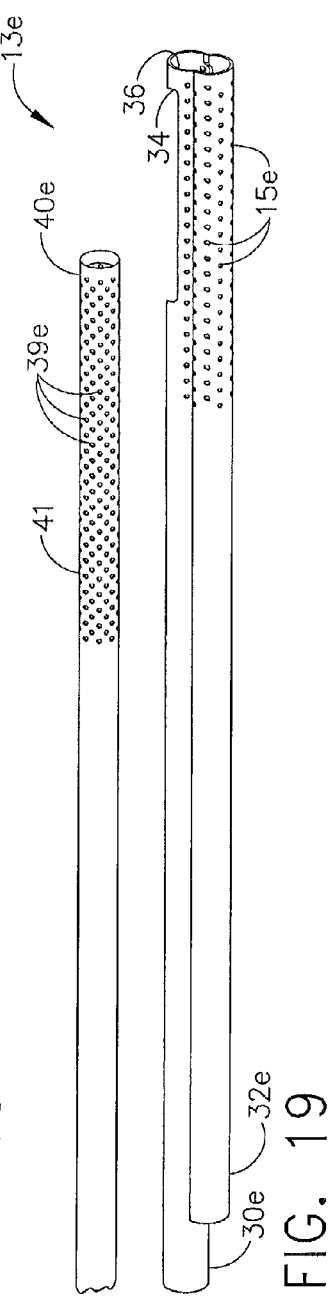
FIG. 19 is an isometric view of yet another additional alternate probe having a plurality of longitudinal rows of reduced diameter external vacuum holes for the disposable probe assembly of FIG. 1 with a piercing tip omitted and a cutter tube detached also having a plurality of longitudinal rows of reduced diameter holes.

In FIG. 19, yet another additional alternate probe 13e has a plurality of longitudinal rows of reduced diameter external vacuum holes 15e. A cutter tube 40e has a plurality of longitudinal rows of reduced diameter cutter holes 39e for assisting in bleeding and fluid management. In addition, the exterior of a probe tube 30e has some of the vacuum holes 15e in addition to those in a vacuum lumen 32e such that reduced diameter cutter holes 39e in the cutter tube 40e may readily communicate externally.

Figure 20:
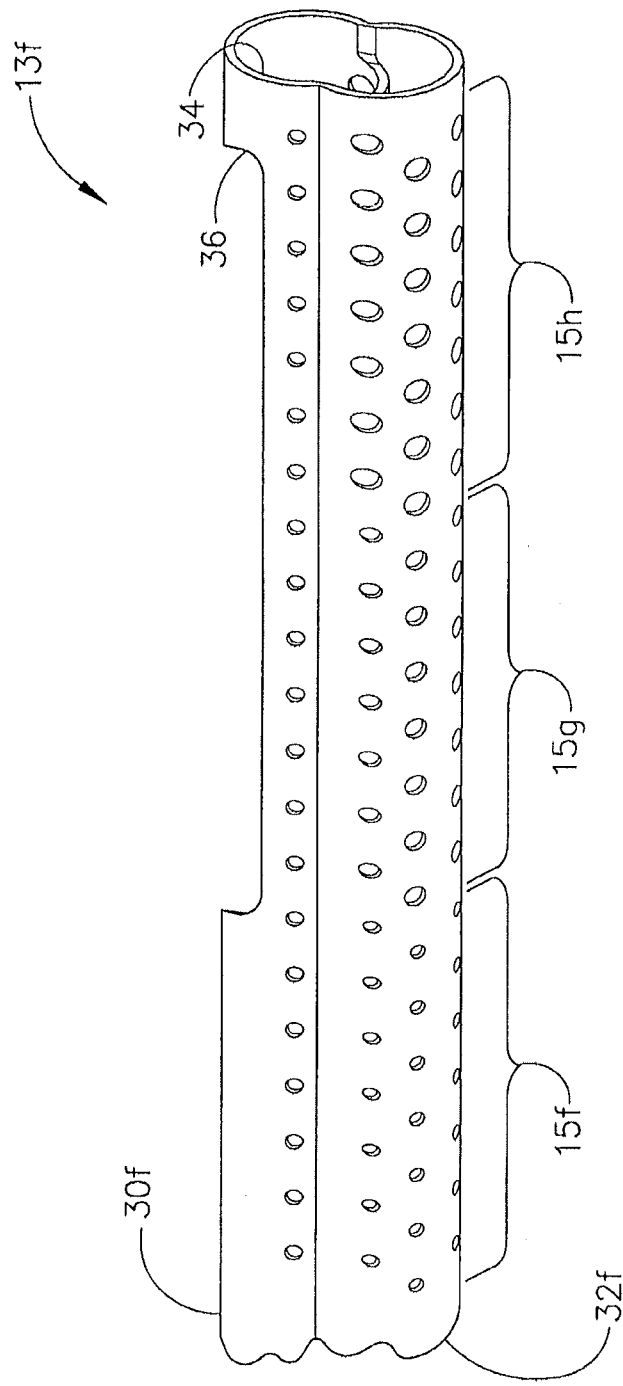
FIG. 20 is an isometric view of yet a further alternative probe having a plurality of longitudinal rows of external vacuum holes with diameters graduated with relation to longitudinal distance along the shaft for the disposable probe assembly of FIG. 1 with a piercing tip omitted.

In FIG. 20, yet a further alternative probe 13f has a plurality of longitudinal rows of graduated diameter external vacuum holes 15f-15h in a probe tube 30f, with the largest external vacuum holes 15h most distal, the smallest external vacuum holes 15f most proximal, and the mid-sized external vacuum holes 15g in between. The cross sectional area of the holes 15f-h are selected to correspond with a typical vacuum pressure drop as a function of longitudinal position on the probe tube 30f, thereby tending to avoid the likelihood of higher vacuum proximally tending to suck in tissue.

Figure 21:
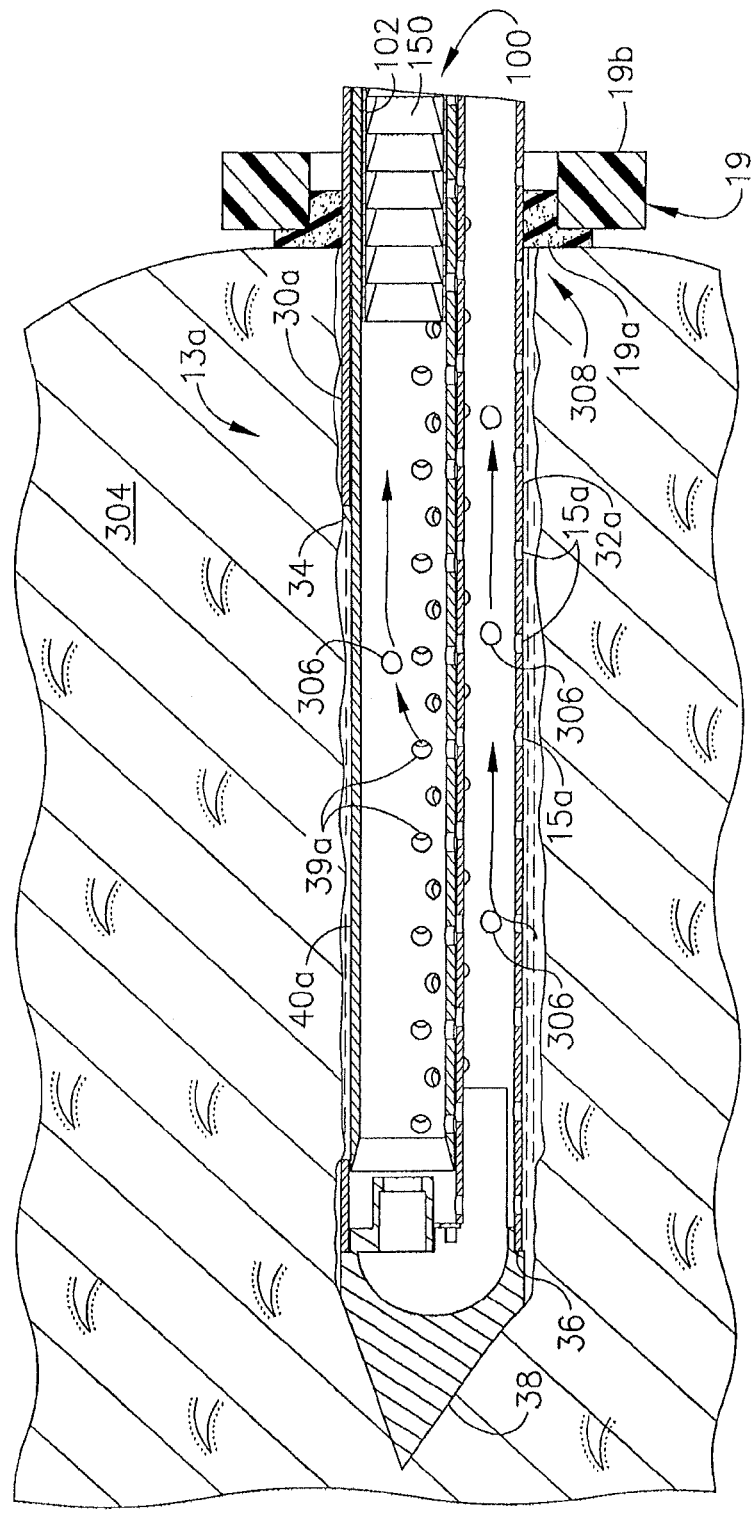
FIG. 21 is a left side view of the probe of FIG. 15 in longitudinal vertical cross section and inserted into tissue with cutter tube advanced to close a side aperture and with a sample retraction straw with internal indicator tube retracted exposing internal vacuum holes partially aligned with external vacuum holes.

In use, in FIG. 21, the probe 13a is inserted into body tissue 304 with a hole formed by the piercing tip 38. The cutter tube 40a is distally advanced to close the side aperture 34 in the probe tube 30a to reduce tissue trauma during insertion. The stacking straw assembly 100 is retracted to an initial position. Vacuum assistance is present through both the cutter tube 40a and the vacuum lumen 32b during insertion, encouraging bodily fluids (e.g., blood) 306 to be drawn into external vacuum holes 15a and additionally into cutter holes 39a being drawn aft for collection, and with a sample retraction straw with internal indicator tube retracted exposing internal vacuum holes partially aligned with external vacuum holes. Bleeding closer to an external opening in skin tissue 308 that is not drawn into the probe 13a is captured into the front absorbent material 19a of the hemostatic disk-shaped ring pad 19 that encompasses and frictionally grips the probe 13a.

Figure 22:
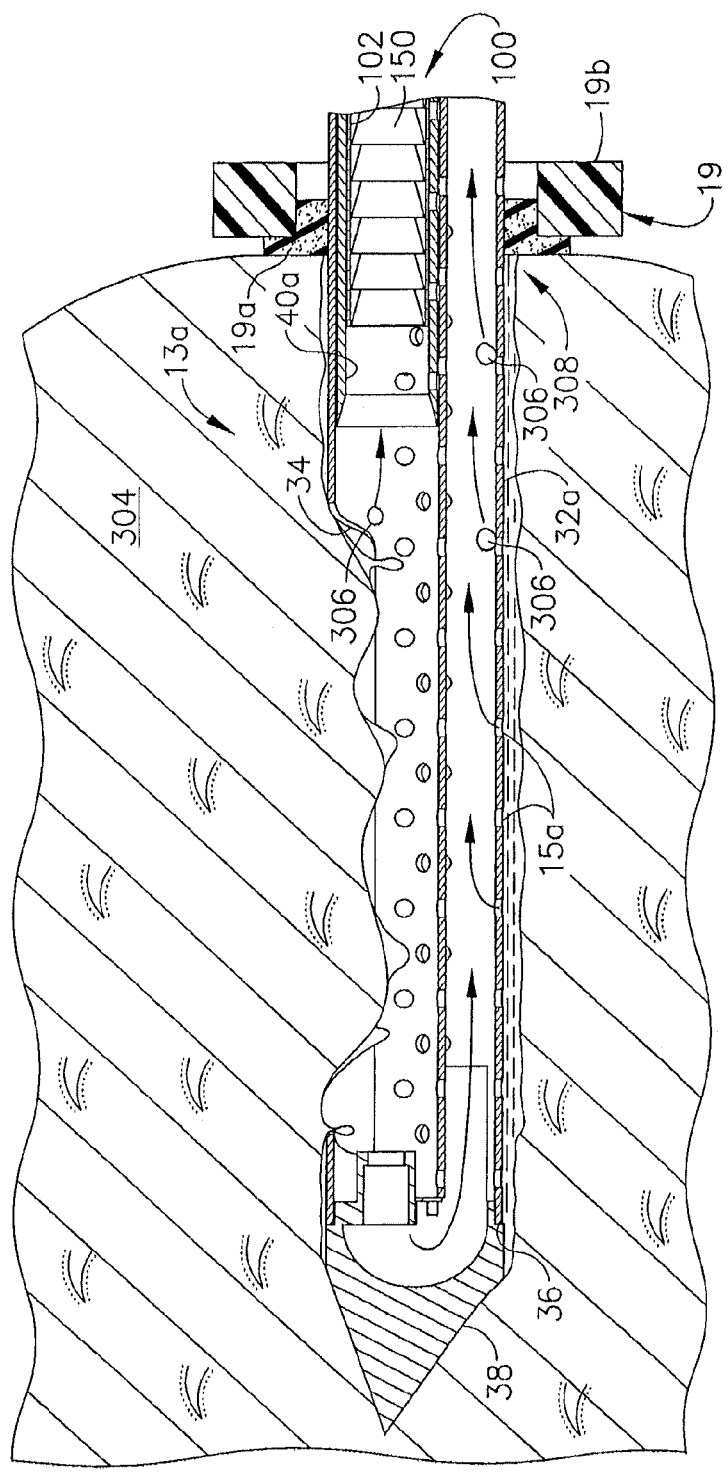
FIG. 22 is a left side view of the probe of FIG. 20 in longitudinal vertical cross section with the cutter tube retracted and vacuum assistance prolapsing tissue into the side aperture and removing bleeding around the probe.
Figure 23:
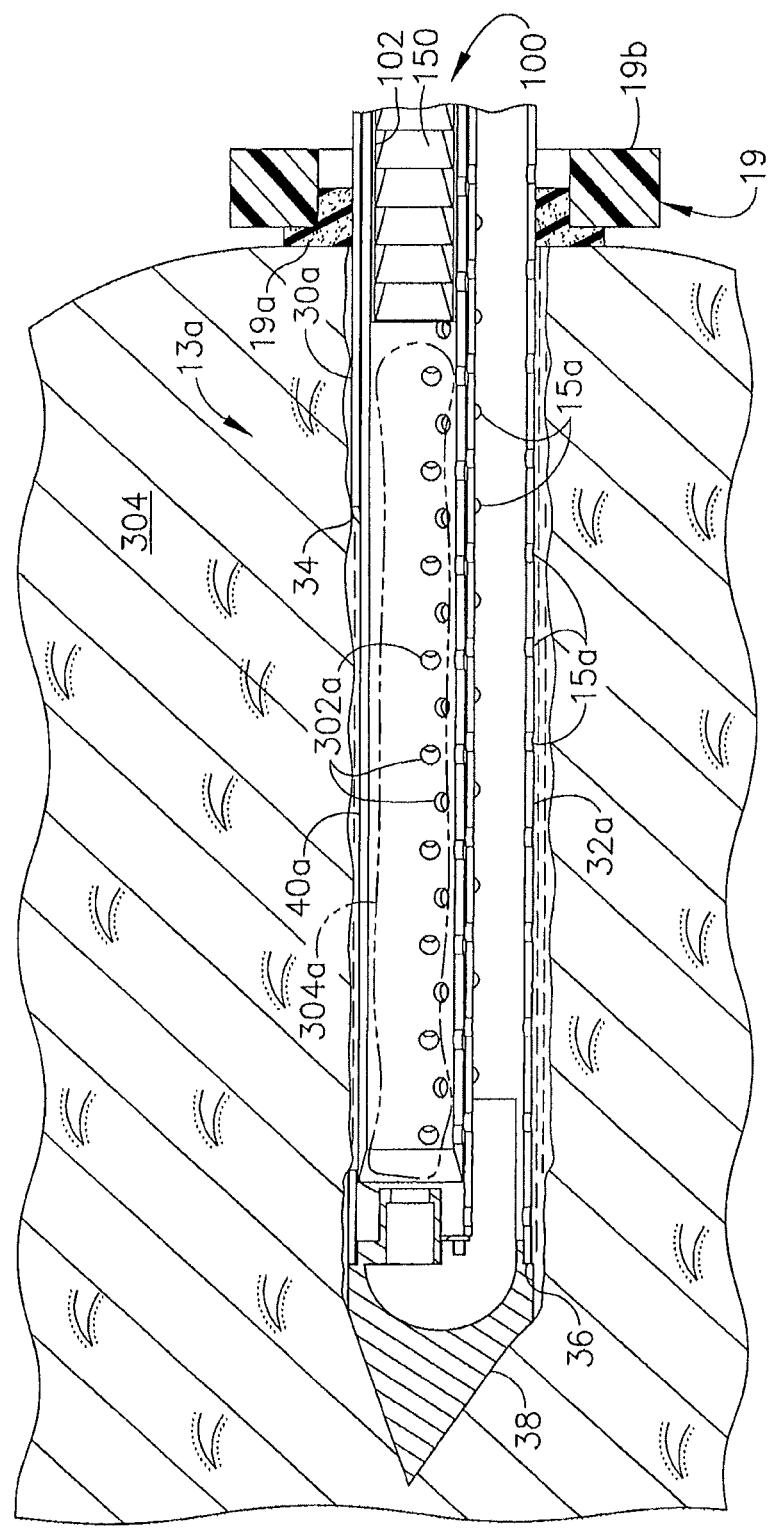
FIG. 23 is a left side view of the probe of FIG. 22 in longitudinal vertical cross section with the cutter tube advanced to sever a tissue sample.
Figure 24:
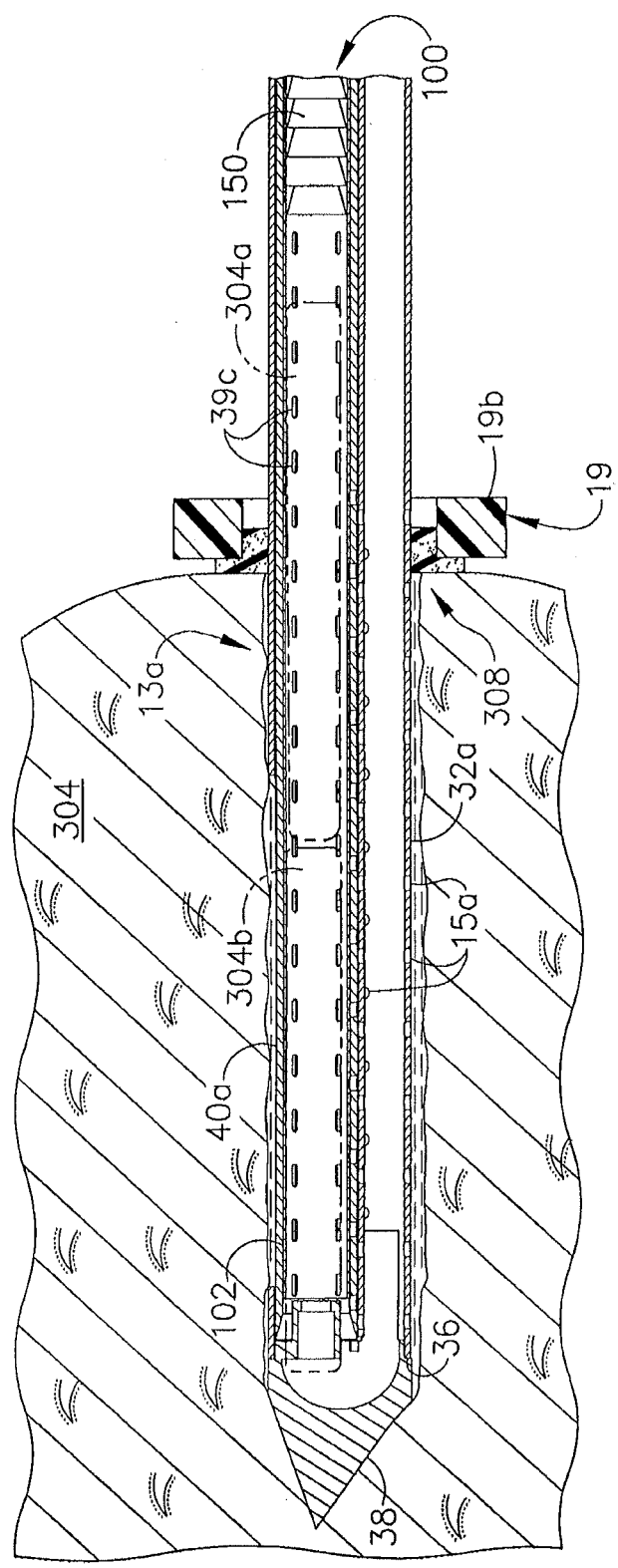
FIG. 24 is a left side view of the probe of FIG. 23 in longitudinal vertical cross section with the cutter tube advanced a second time severing a second tissue sample with a sample retraction straw advanced within the cutter tube to capture both tissue samples, the latter urging the indicator tube aft.

In FIG. 22, the cutter tube 40a is retracted, allowing vacuum assistance from both the cutter tube 40a and vacuum lumen 32a to prolapse tissue 304 into the side aperture 34 of the probe tube 30a. In FIG. 23, distal advancement of the cutter tube 40a has resulted in severing of a first tissue sample 304a encompassed therein. In FIG. 24, the elongate straw 102 has been distally advanced within the cutter tube 40a, which in the interim has been reciprocated another time, to encompass and capture the first tissue sample 304a as well as a second tissue sample 304b which has been severed in the interim by another reciprocation of the cutter tube 40a. The presence of the tissue samples 304a, 304b in the elongate straw 102 extrudes aft the indicator straw 150.

Figure 25:
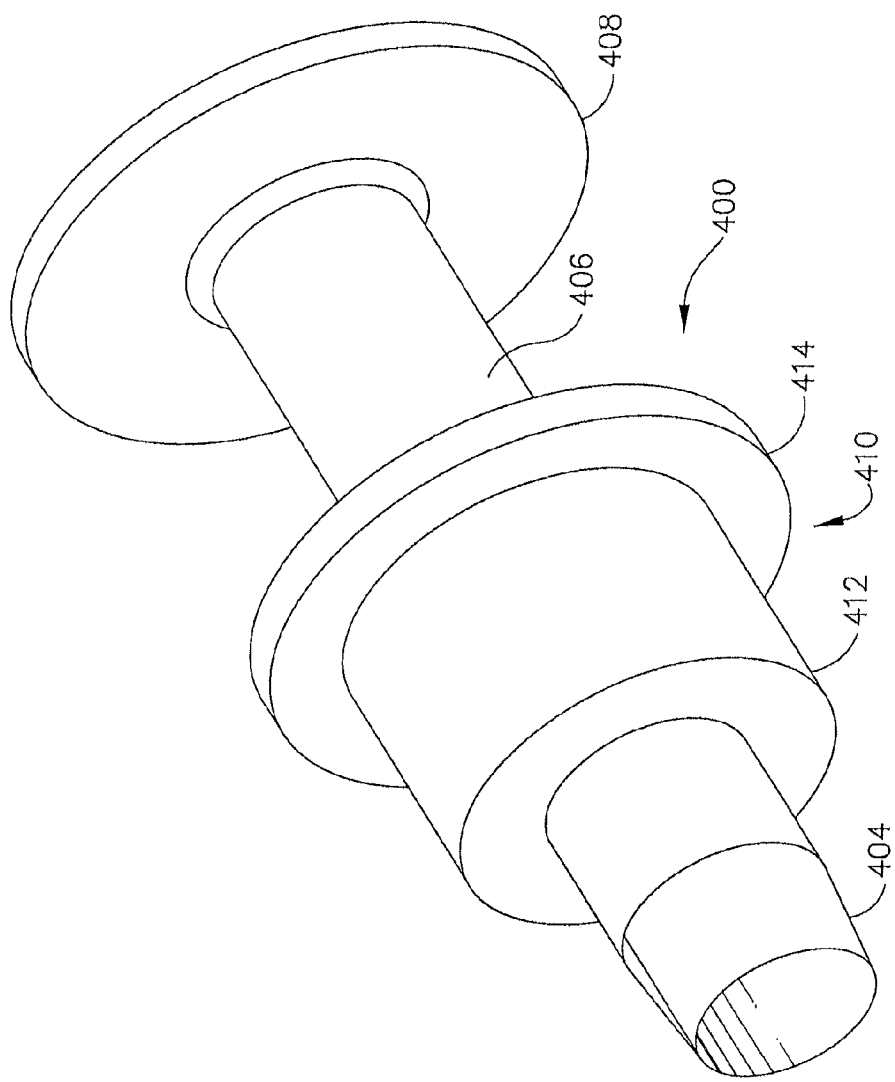
FIG. 25 is an isometric short aperture sleeve with adjustable hemostatic ring for the biopsy device of FIG. 1.
Figure 26:
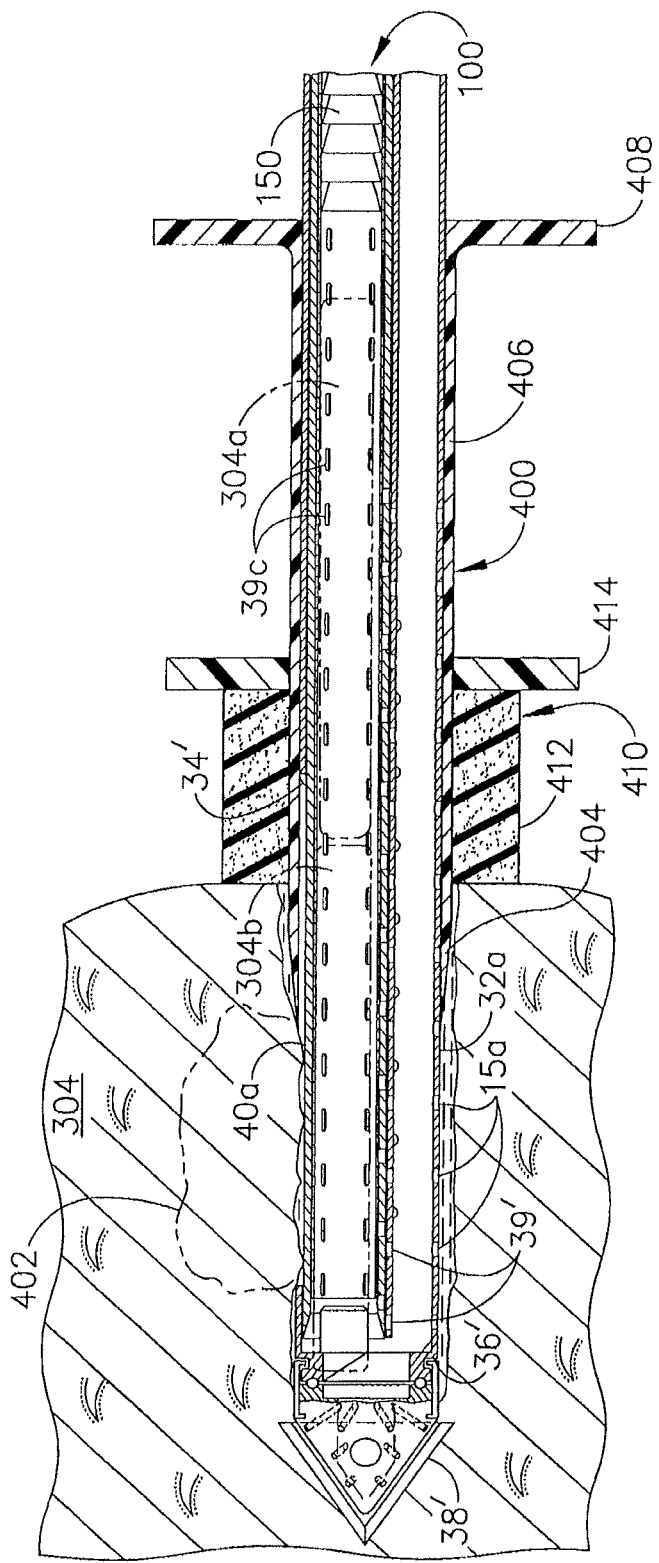
FIG. 26 is a left side view of the probe of FIG. 6 in longitudinal cross section with the cutter tube advanced to sever a second tissue sample close to the skin with a side aperture sleeve with adjustable hemostatic ring to avoid skin gouging by the cutter tube.

In FIGS. 25-26, a sleeve 400 advantageously assists in bleeding control as well as enabling the taking of biopsy samples of a lesion 402 close to the surface wherein the side aperture 34 is partially exposed. A taper distal end 404 of a cylindrical tube 406 of the sleeve 400 may be longitudinally positioned by gripping a pushing a proximal disk flange 408. In FIG. 26, the sleeve 400 has been slid overtop of the exposed portion of the side aperture 34' of the probe 13f so that the cutter 40a doesn't gouge skin as it translates from outside of the body across the side aperture 34'. The sleeve 400 may further plug the external opening in the skin to further reduce external bleeding, not only with its increased diameter of the cylindrical tube 406 but also by positioning a hemostatic ring 410. To that end, an absorbent ring 412 frictionally engages the cylindrical tube 406. To assist in positioning the absorbent ring 412, a rigid backplane 414 attached proximally to the absorbent ring 412 may be included for moving the hemostatic ring 412 into contact with the skin.

While preferred embodiments of the present invention have been shown and described herein, it will be obvious to those skilled in the art given the benefit of the present disclosure that such embodiments are provided by way of example only. Numerous variations, changes, and substitutions will now occur to those skilled in the art without departing from the spirit and scope of the appended claims. Additionally, each element described in relation to the invention may be alternatively described as a means for performing that element's function.

For example, bleeding and fluid management may be enhanced by flushing the external vacuum holes 15 to remove tissue debris and coagulated blood, such as described in the co-pending and commonly-owned U.S. patent application Ser. No. 11/344,879, "Biopsy Device with Replaceable Probe Incorporating Static Vacuum Source Dual Valve Sampling Stacking Retrieval and Saline Flush" to Hibner, filed 1 Feb. 2006, the disclosure of which is hereby incorporated by reference in its entirety.

For another example, in some applications a sleeve with a piercing tip or a sleeve with an open distal end closed by an introducer stylet (not shown) are used to penetrate tissue prior to insertion of a probe of a biopsy device for taking the biopsy samples. Consistent with aspects of the present invention, pneumatic fluid passages may be formed in the sleeve and/or introducer stylet that communicate proximally with a vacuum source for bleeding and fluid management. In addition, a hemostatic disc-shaped ring pad may be added to the sleeve to further assist in preventing or obscuring external bleeding.

As an additional example, while a fixed ratio translation/rotation cutter tube 40 is depicted herein, applications consistent with the present invention may not rotate the cutter tube or selectively rotate the cutter tube to present sampling holes to the side aperture or to a hole in an encompassing probe tube to assist in bleeding/fluid management. Rotating these holes to be blocked during other portions of the procedure may then enhance the available suction for retraction of a tissue sample, for instance.

We claim:

1. A biopsy device, comprising:
   (a) an elongate needle defining an internal passage, the elongate needle having a distal end;
   (b) a proximal portion attached to the elongate needle positionable to insert the elongate needle into tissue;
   (c) a cutter defining a lumen, a distal opening, and a first plurality of openings in communication with the internal passage of the elongate needle, wherein the cutter is received by the elongate needle to sever a tissue sample received in the elongate needle; and
   (d) a vacuum conduit attached to the proximal portion in communication with the internal passage and configured to be coupled to a vacuum source.

2. The biopsy device of claim 1, wherein the elongate needle further comprises a lateral lumen adjacent to the cutter and defining the internal passage.

3. The biopsy device of claim 1, wherein the elongate needle further comprises a side aperture sized to admit prolapsed tissue, wherein the cutter is reciprocally received within by the elongate needle and is axially offset within the elongate needle to closely reciprocate past the side aperture.

4. The biopsy device of claim 1, wherein the elongate needle comprises a second plurality of openings along an exterior surface of the elongate needle in communication with the internal passage, the second plurality of openings being sized to admit fluid and to resist prolapse of tissue.

5. The biopsy device of claim 4, wherein the elongate needle further comprises a plurality of dimples along the exterior surface of the elongate needle, wherein the each opening of the second plurality of openings are positioned within a dimple of the plurality of dimples.

6. The biopsy device of claim 4, wherein the second plurality of openings are adjacent to the first plurality of openings when the cutter is in a distal position.

7. The biopsy device of claim 4, wherein the first and second plurality of openings comprise a plurality of longitudinal rows.

8. The biopsy device of claim 4, wherein the first and second plurality of openings comprise a first and second plurality of slots.

9. The biopsy device of claim 8, wherein the first plurality of slots are arranged transversely along the cutter, wherein the second plurality of slots are arranged transversely along the elongate needle.

10. The biopsy device of claim 8, wherein the first plurality of slots are arranged in a spiraled configuration along the cutter, wherein the second plurality of slots are arranged in a spiraled configuration along the elongate needle.

11. The biopsy device of claim 4, wherein the second plurality of openings comprise a plurality of longitudinal rows, wherein the diameter of each opening of the second plurality of openings gradually increases along each row of the plurality of longitudinal rows.

12. The biopsy device of claim 1 further comprising a vacuum canister, wherein the vacuum conduit is configured to be in communication with the vacuum canister.

13. The biopsy device of claim 1 further comprising a tip at the distal end of the elongate needle.

14. The biopsy device of claim 13, wherein the tip comprises a second plurality of openings in communication with the internal passage, the plurality of openings being sized to admit fluid and to resist prolapsed of tissue.

15. The biopsy device of claim 14, wherein the tip comprises a conical portion and a blade portion, wherein the blade portion is secured to the conical portion.

16. The biopsy device of claim 15, wherein the second plurality of openings are formed through the conical portion.

17. The biopsy device of claim 13, wherein the tip is rotatable relative to the elongate needle.

18. The biopsy device of claim 1, further comprising a reusable handpiece releasably coupled with a disposable probe.

19. A biopsy device, comprising:
(a) an elongate needle defining an internal passage, the elongate needle having a distal end;
(b) a proximal portion attached to the elongate needle positionable to insert the elongate needle into tissue;
(c) a cutter received by the elongate needle to sever a tissue sample received in the elongate needle;
(d) a vacuum conduit attached to the proximal portion in communication with the internal passage and configured to be coupled to a vacuum source; and
(e) a plurality of openings along an exterior surface of the elongate needle in communication with the internal passage, the plurality of openings being sized to admit fluid and to resist prolapse of tissue;
wherein the biopsy device is operable to communicate one or more severed tissue samples proximally through the cutter, relative to the elongate needle and relative to the cutter.

20. A biopsy device, comprising:
(a) an elongate needle defining an internal passage, the elongate needle having a distal end;
(b) a proximal portion attached to the elongate needle positionable to insert the elongate needle into tissue;
(c) a cutter received by the elongate needle to sever a tissue sample received in the elongate needle, wherein the cutter comprises a cutter tube, wherein the cutter tube comprises a plurality of openings in communication with the internal passage of the elongate needle; and
(d) a vacuum conduit attached to the proximal portion in communication with the internal passage and configured to be coupled to a vacuum source.

* * * * *